United States Patent
Tani et al.

(10) Patent No.: US 9,566,307 B2
(45) Date of Patent: Feb. 14, 2017

(54) PHARMACEUTICAL COMPOSITION

(71) Applicant: Kyushu University, National University Corporation, Fukuoka (JP)

(72) Inventors: Kenzaburo Tani, Fukuoka (JP); Hiroyuki Inoue, Fukuoka (JP); Keisuke Yasunari, Fukuoka (JP); Shohei Miyamoto, Fukuoka (JP)

(73) Assignee: KYUSHU UNIVERSITY, NATIONAL UNIVERSITY CORPORATION, Fukuoka-Shi, Fukuoka (JP)

( * ) Notice: Subject to any disclaimer, the term of this patent is extended or adjusted under 35 U.S.C. 154(b) by 0 days.

(21) Appl. No.: 14/395,513

(22) PCT Filed: Apr. 19, 2013

(86) PCT No.: PCT/JP2013/061686
§ 371 (c)(1),
(2) Date: Oct. 20, 2014

(87) PCT Pub. No.: WO2013/157648
PCT Pub. Date: Oct. 24, 2013

(65) Prior Publication Data
US 2015/0297650 A1    Oct. 22, 2015

(30) Foreign Application Priority Data

Apr. 19, 2012  (JP) ................. 2012-096088

(51) Int. Cl.
| | | |
|---|---|---|
| A61K 35/768 | (2015.01) | |
| A61K 45/00 | (2006.01) | |
| A61K 38/16 | (2006.01) | |
| A61K 45/06 | (2006.01) | |
| C12N 15/01 | (2006.01) | |

(52) U.S. Cl.
CPC ........... *A61K 35/768* (2013.01); *A61K 38/162* (2013.01); *A61K 45/00* (2013.01); *A61K 45/06* (2013.01); *C12N 2770/32011* (2013.01)

(58) Field of Classification Search
CPC .......... A61K 35/768; A61K 2300/00
See application file for complete search history.

(56) References Cited

U.S. PATENT DOCUMENTS

2006/0275262 A1*  12/2006  Mathis ............... A61K 48/0058
424/93.2

FOREIGN PATENT DOCUMENTS

| JP | 2007-527719 A | 10/2007 |
|---|---|---|
| JP | 2009-507823 A | 2/2009 |
| JP | 2012-46489 A | 3/2012 |
| WO | 2011/054620 A1 | 5/2011 |

OTHER PUBLICATIONS

Berry et al. The prostate, 2008, vol. 68, pp. 577-587.*
Oberste et al. J. Virol. 1999, vol. 73 (3), pp. 1941-1948.*
Kelly EJ et al., Engineering microRNA responsiveness to decrease virus pathogenicity, Nat Med, 2008, 14, 1278-1283.
Trallero G et al., Enteroviruses in Spain over the decade 1998-2007: virological and epidemiogical studies, J Clin Virol, 2010, 47, 170-176.
Haley, E. S., et al., Regional administration of oncolytic Echovirus 1 as a novel therapy for the peritoneal dissemination of gastric cancer. J. Mol. Med., 2009, vol. 87, No. 4, pp. 385-399.
Yasunari, K., et al., Oncolytic Echovirus 4 as a Potent Virotherapy Agent Against Human Esophageal Squamous Cell Carcinoma., Molecular Therapy, 2012. 05, vol. 20, No. Suppl. 1, pp. S273-S274, col. 707.

* cited by examiner

*Primary Examiner* — Bao Li
(74) *Attorney, Agent, or Firm* — Enshan Hong; VLP Law Group LLP

(57) ABSTRACT

A pharmaceutical composition contains a coxsackievirus A11 type that infects cancer cells or an echovirus 4 type that infects cancer cells. The coxsackievirus A11 type and the echovirus 4 type may have capsid eliminated. The pharmaceutical composition has an intensive cytotoxicity to a cell of cancer selected from the group consisting of small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, breast cancer, cervical cancer, and pancreatic cancer, which is the cancer cells of a solid cancer.

15 Claims, 14 Drawing Sheets

PHARMACEUTICAL COMPOSITION

PRIORITY CLAIM

This is a U.S. national stage of application No. PCT/JP2013/061686, filed on Apr. 19, 2013. Priority is claimed on the following applications: Country: Japan, Application No.: 2012-096088, Filed: Apr. 19, 2012), the content of which is incorporated here by reference

SEQUENCE LISTING

The instant application contains a Sequence Listing which has been submitted electronically in ASCII format and is hereby incorporated by reference in its entirety. Said ASCII copy, created on Dec. 22, 2014, is named Revised_QP120013_ST25.txt and is 13,474 bytes in size.

TECHNICAL FIELD

The present disclosure relates to a pharmaceutical composition containing tumor lysis enteroviruses.

BACKGROUND ART

Malignant tumor is a primary cause of death for Japanese, and in the face of statistics, one out of three people dies due to malignant tumor. The long time efforts dramatically have improved the results of operative therapy, radiation therapy, chemotherapy, and molecular targeted drugs against malignant tumors. However, the death rate caused by malignant tumor is still high, and there is a need for the development of novel therapeutical modality effective for malignant tumors.

Oncolytic virus therapy as a new therapy method is getting attention because of its direct cytocidal effect. For example, several clinical trials utilizing oncolytic adenoviruses and herpes simplex viruses that are DNA viruses have been carried out for treatment of brain tumor and breast cancer, with the published results demonstrating their safeness and anticancer efficacy.

On the other hand, enteroviruses of Picornaviridae that are RNA viruses have no genome integration in host cells after infection, have little risk of malignant transformation due to the gene mutation, and have no oncogene, thus possessing a relatively higher safety to human beings. Still further, enteroviruses have a fast growth rate in cells, and thus are expected to show a quick and high oncolytic effect.

For example, Patent Literature 1 discloses oncolytic virotherapy utilizing enteroviruses such as coxsackievirus (CV) A21 (CVA21) type, echovirus (EV) 6 (EV6) type, EV7 type, EV11 type, EV12 type, EV13 type, and EV29 type. In addition, Patent Literature 2 discloses oncolytic virotherapy utilizing enteroviruses such as CVA13 type, CVA15 type, CVA18 type, CVA21 type, EV1 type, EV7 type, EV8 type, and EV22 type.

CITATION LIST

Patent Literature

Patent Literature 1: National Patent Publication No. 2007-527719
Patent Literature 2: Unexamined Japanese Patent Application Kokai Publication No. 2012-46489

Non Patent Literature

Non-patent Literature 1: Kelly E J et al. Engineering microRNA responsiveness to decrease virus pathogenicity, Nat Med, 2008, 14, 1278-1283
Non-patent Literature 2: Trallero G et al. Enteroviruses in Spain over the decade 1998-2007: virological and epidemiological studies, J Clin Virol, 2010, 47, 170-176

SUMMARY OF INVENTION

Technical Problem

However, there is a report that CVA21 type caused an administered mouse to have a serious muscle inflammation, indicating a high fatality rate (see Non-patent Literature 1). In addition, EV6 type, EV11 type, and the like are reported as causal viruses of aseptic meningitis (see Non-patent Literature 2). Still further, there is no report so far confirming the safeness in clinical trials regarding the above-explained tumor oncolytic virotherapy utilizing enteroviruses. In view of those facts, it is so far difficult to confirm a sure safeness of the oncolytic virotherapy utilizing enteroviruses.

The present disclosure has been made in view of the aforementioned circumstances, and it is an objective of the present disclosure to provide a pharmaceutical composition containing safer enteroviruses.

Solution to Problem

The inventor of the present disclosure carried out screening tests using over 30 kinds of enteroviruses and multiple kinds of human malignant tumor cell lines to identify promising enteroviruses that have safer profile. As a result, they demonstrated that EV4 type and CVA11 type that had not been reported until now showed a high cytotoxicity. Both viruses may be detected from patients with aseptic meningitis, but the frequency thereof is equal to or smaller than 1.0% of all viruses detected, which is quite low in comparison with other EVs such as EV6 type and EV11 type. Therefore, both viruses can be considered as safer viruses.

That is, a pharmaceutical composition according to a first aspect of the present disclosure contains a coxsackievirus A11 type that infects cancer cells or an echovirus 4 type that infects cancer cells.

In this case, the coxsackievirus A11 type or the echovirus 4 type may have capsid eliminated.

The aforementioned pharmaceutical composition may be applied together with a phosphoinositol-3-kinase inhibitor.

The aforementioned pharmaceutical composition may be applied together with an MAP kinase kinase inhibitor.

The aforementioned pharmaceutical composition may be applied together with an anticancer agent.

The aforementioned pharmaceutical composition may be utilized for a therapy of a CDDP resistant cancer.

The aforementioned pharmaceutical composition may contain the coxsackievirus A11 type, and be utilized for a therapy of a gefitinib resistant or oxaliplatin resistant cancer.

The aforementioned pharmaceutical composition may contain the coxsackievirus A11 type, in which the cancer cells may be cancer stem cells.

The aforementioned pharmaceutical composition may contain the coxsackievirus A11 type, in which the cancer cells may be human cancer cells selected from the group consisting of small cell lung cancer, non-small cell lung cancer, malignant mesothelioma, colorectal cancer, colon/rectum cancer, esophageal cancer, hypopharynx cancer, human-B-lymphocyte tumor, breast cancer, and cervical cancer.

The aforementioned pharmaceutical composition may contain the echovirus 4 type, in which the cancer cell may be a cell of cancer selected from the group consisting of small cell lung cancer, non-small cell lung cancer, colorectal cancer, colon/rectum cancer, pancreatic cancer, and esophageal cancer.

A pharmaceutical composition according to a second aspect of the present disclosure contains a nucleic acid derived from a coxsackievirus A11 type that infects cancer cells or a nucleic acid derived from an echovirus 4 type that infects cancer cells.

Advantageous Effects of Invention

According to the present disclosure, since what is contained is CVA11 type or EV4 type having low pathogenicity to human being, it becomes possible to further ensure the safeness of a pharmaceutical composition utilizing enteroviruses.

DESCRIPTION OF EMBODIMENTS

First Embodiment

Figure 1:
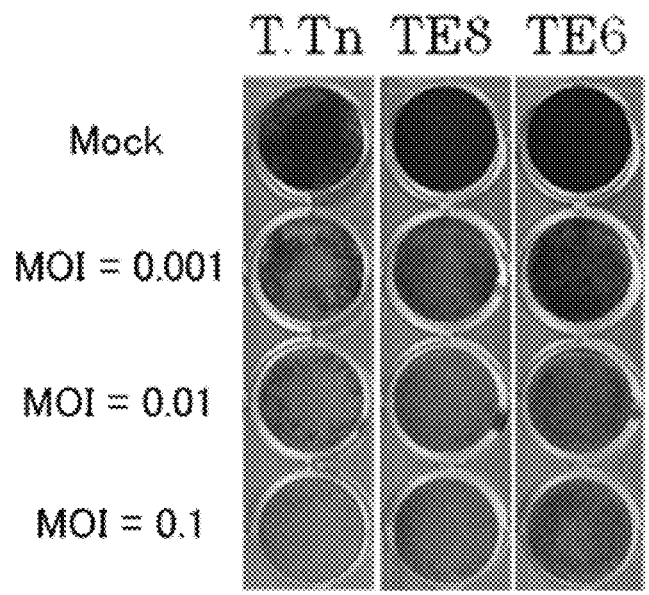
FIG. 1 is a diagram illustrating a cytotoxicity of EV4 type against a cell line of esophageal cancer.

A first embodiment of the present disclosure will be explained in detail. A pharmaceutical composition of this embodiment contains CVA11 type that infects cancer cells or EV4 type that infects cancer cells. CVA11 type and EV4 type can infect cells by being bound with virus receptors of a cell surface. Example known virus receptors are decal acceleration factor (DAF or CD55), intercellular molecule-1 (ICAM-1 or CD54), and integrin $\alpha_2\beta_1$ (CD49b). When CVA11 type and EV4 type mutually act with the virus receptors, the capsid of CVA11 type and that of EV4 type are de-stabilized. This induces the uncoating of CVA11 type and that of EV4 type.

CVA11 type and EV4 type can be isolated from a sample and the like through conventionally well-known virus isolation techniques. Example virus isolation techniques are centrifugal separation and virus breeding by cultured cells.

CVA11 type and EV4 type can be subjected to a biological screening by successively cultivating viruses present in a nature in cell lines through multiple generations so as to accomplish a high infectiveness to cancer cells. Example cell lines suitable for biological screening are cancer cell lines that express DAF, ICAM-1, and integrin $\alpha_2\beta_1$.

CVA11 type and EV4 type may be ones present in a nature or may be altered ones. An example altered CVA11 type and EV4 type is CVA11 type and EV4 type with their capsid eliminated. Capsid can be eliminated by a process of protease, such as chymotrypsin or trypsin. More specifically, when CVA11 type or EV4 type are processed with chymotrypsin in the present of a surfactant agent like alkyl sulfate, capsid can be eliminated. When the capsid of CVA11 type and that of EV4 type are eliminated, the virus infectiveness to a cancer cell can be increased. In addition, because proteins present in capsid is a major factor of the humoral reaction of a host and the cellular reaction thereof, when the capsid of CVA11 type and that of EV4 type are eliminated, the immunological response of the host can be reduced.

The kind of cancers that is the target of the pharmaceutical composition containing CVA11 type or EV4 type is not limited to any particular kind, and includes solid cancers and hematological malignancies. CVA11 type and EV4 type have a cytotoxicity against solid cancers and hematological malignancies. The cytotoxicity by CVA11 type and EV4 type is based on dissolution of cancer cells when the virus infects them and is replicated in the cell cytoplasm, and partially on the resultant caspases-dependent apoptosis in the cancer cells.

The cytotoxicity of CVA11 type and EV4 type can be confirmed by evaluating the survival rates of the cancer cell lines infected with CVA11 type or EV4 type. Example techniques of testing the survival of the cell lines are experiments of staining a fixed cell with a stain solution, and of quantitating the cell number of stained living cells, a crystal violet assay, and a technique of quantitating apoptosis-specific markers. As to the cell lines of cancer having undergone incubation with CVA11 type or EV4 type, when the cancer cells surviving after a predetermined time are quantitated through the aforementioned techniques, as a result, the killed cancer cells by the cytotoxicity due to the infection with CVA11 type or EV4 type can be quantitated.

CVA11 type and EV4 type have a cytotoxicity to the cell lines including solid cancers and hematological malignancies, but the types of solid cancer cells with a remarkably intensive anticancer cytotoxicity is cancer groups consisting of small cell lung cancer, non-small cell lung cancer, colorectal cancer, colon/rectum cancer, and esophageal cancer. When the pharmaceutical composition contains CVA11 type, it is preferable that such a pharmaceutical composition should be applied to cancer cells selected from the groups consisting of small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, breast cancer, and cervical cancer. Conversely, when the pharmaceutical composition contains EV4 type, it is preferable that the pharmaceutical composition should be applied to cancer cells selected from the group consisting of small cell lung cancer, non-small cell lung cancer, colorectal cancer, colon/rectum cancer, pancreatic cancer, and esophageal cancer.

The pharmaceutical composition of this embodiment may contain, in addition to CVA11 type or EV4 type, a carrier, a diluent agent, or an adjuvant, and the like. Example preferable carriers are liposome, and micelle. Liposome includes steroid or a combination with a steroid precursor contributing to fat and the membrane stability. In this case, example fats are phosphatidyl compounds, such as phosphatidylglycerol, phosphatidylcholine, phosphatidylserine, sphingolipid, phosphatidylethanolamine, cerebroside, and ganglioside. CVA11 type and EV4 type coated with liposome or micelle reduce the immunological response of a host.

Example diluent agents are desalted water, diluted water, and psychological saline. In addition, example adjuvants are plant oil, a cellulose derivative, polyethylene glycol, and fatty acid ester.

The pharmaceutical composition of this embodiment can be administered through various techniques. For example, it is preferable to administer the pharmaceutical composition through intratumoral administration, intravenous administration, and intraperitoneal administration in accordance with the kind of cancer. In particular, in many cases of esophageal cancer, colorectal cancer, and the like, the pharmaceutical composition can be directly injected to tumor tissues while visually checking the tumor tissue through an endoscope or the like. In this case, since the injected tumor site can be checked through the endoscope or the like, there is an advantage that it is easy to cope with accidental bleeding. Note that the pharmaceutical composition can be administered orally, or may be administered through a muscle, a skin, a rectum, a vagina, a nose, and the like. In the case of oral administration, the pharmaceutical composition may contain a sweeting agent, a disintegrating agent, a diluent agent, a coating agent, a preserving agent, and the like.

The pharmaceutical composition of this embodiment is administered in such a way that CVA11 type or EV4 type becomes a sufficient amount to cure cancer. The dosage amount is determined in accordance with the body weight of a patient, age, gender, the size of a tumor tissue, and the like. When, for example, the pharmaceutical composition is applied as a liquid medication, it is appropriate if CVA11 type or EV4 type be contained by $1 \times 10^2$ to $1 \times 10^{10}$ plaque-formation unit in the liquid medication of 1 ml. It is preferable that CVA11 type or EV4 type should be contained in the liquid medication of 1 ml by equal to or greater than $1 \times 10^5$ plaque-formation unit. The number of administrations of the pharmaceutical composition may be one or multiple times. In addition, the pharmaceutical composition may be continuously administrated as a slow-release formulation.

The pharmaceutical composition of this embodiment may be applied together with a phosphoinositol-3-kinase (PI3K) inhibitor. The PI3K inhibitor inhibits the activity of enzyme that phosphorylates the hydroxyl group at the 3-position of inositol ring of inositol phosphatide. As is demonstrated in the following examples, when applied together with PI3K inhibitor, CVA11 type and EV4 type have the cytotoxicity to cancer cells enhanced. Various compounds have been developed as the PI3K inhibitor, and a commercially available one may be applied or one obtained by synthesis may be applied.

The pharmaceutical composition of this embodiment may be applied together with an MAP kinase kinase inhibitor. The MAP kinase kinase inhibitor inhibits the activity of enzyme that phosphorylates the MAP kinase at the downstream of G protein in an intracellular signal transducing system. As is demonstrated in the following examples, when applied together with the MEK inhibitor (MAP kinase kinase inhibitor), CVA11 type and EV4 type have the cytotoxicity to cancer cell enhanced. Various compounds have been developed as the MAP kinase kinase inhibitor, and a commercially available one may be applied or one obtained by synthesis may be applied.

The PI3K inhibitor and the MAP kinase kinase inhibitor applied together can be administered through various techniques. For example, it is preferable to administer the pharmaceutical composition through intratumoral administration, intravenous administration, and intraperitoneal administration in accordance with the kind of cancer. The dosage amount of the PI3K inhibitor and that of the Map kinase kinase inhibitor applied together are determined in accordance with the body weight of a patient, age, gender, the size of a tumor tissue, and the like. For example, the respective dosage amounts of the PI3K inhibitor and the MAP kinase kinase inhibitor are determined appropriately in accordance with the gender of a patient, age, body weight, a symptom, and the like. In the case of intravenous injection, the dosage amount is 0.0001 mg/kg to 100 mg/kg per a day in the case of an adult. In this case, the PI3K inhibitor and the MAP kinase kinase inhibitor may be administrated at once or several times, and in the case of multiple administrations, such inhibitors may be administrated successively. In the case of oral administration, the respective dosage amounts are 0.001 mg/kg to 1000 mg/kg per a day in the case of an adult. Note that the amount out of the aforementioned ranges may be adopted as needed.

The pharmaceutical composition of this embodiment may be applied together with an anticancer agent. The anticancer agent is not limited to any particular one, but the anticancer agent utilized for the therapy of small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, cervical cancer, pancreatic cancer and the like. Specific examples of the anticancer agent are CDDP (cisplatin), gefitinib, and oxaliplatin.

In addition, the pharmaceutical composition of this embodiment may be utilized for the therapy of a CDDP resistant cancer. The CDDP resistant cancer is a cancer symptom that does not show a reduction of a tumor volume, a suppression of the increase thereof, an improvement and the like of a condition relevant to the cancer even if, for example, the CDDP by a dosage that can accomplish a clinical effectiveness is administered. The kind of CDDP resistant cancer is not limited to any particular one, but examples thereof are small cell lung cancer, non-small cell lung cancer, lung squamous cell carcinoma, malignant mesothelioma, colorectal cancer, colon/rectum cancer, hypopharynx cancer, human-B-lymphocyte tumor, cervical cancer, pancreatic cancer and the like. In particular, as the kind of the CDDP resistant cancer, esophageal cancer is suitable.

When containing CVA11 type, the pharmaceutical composition of this embodiment may be utilized for the therapy of gefitinib resistant or oxaliplatin resistant cancer. The kind of gefitinib resistant or oxaliplatin resistant cancer is not limited to any particular one, but examples of such a kind are small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, cervical cancer, pancreatic cancer and the like.

Still further, as is demonstrated in the following examples, CVA11 type shows an intensive cytotoxicity to a cancer stem cell. Hence, when containing CVA11 type, the pharmaceutical composition of this embodiment may be applied in particular to a cancer stem cell. The cancer stem cells can be identified by checking the expression of, for example, CD133, one of known cancer stem cell markers.

As explained above in detail, according to the pharmaceutical composition of this embodiment, since CVA11 type or EV4 type having a low pathogenicity to human being is utilized, it becomes possible to further enhance the safeness of the pharmaceutical composition utilizing enterovirus.

In addition, CVA11 type and EV4 type according to this embodiment may have capsid eliminated. This enhances the infectiveness of virus to a cancer cell, and decreases the immunological response of a host. As a result, the infectiveness of CVA11 type and EV4 type to a cancer cell can be improved, thereby improving the cytotoxicitycytotoxicity of the pharmaceutical composition to the cancer cell.

Still further, the pharmaceutical composition of this embodiment can be directly administered to a tumor tissue regarding a solid cancer formed in an organ or a tissue. This enhances the infectiveness of CVA11 type and EV4 type to a cancer cell, and thus a further intensive therapy effect can be expected.

Yet further, the kind of cancer cells with higher susceptibility to the pharmaceutical composition of this embodiment is cancer types selected from the groups consisting of small cell lung cancer, non-small cell lung cancer, colorectal cancer, colon/rectum cancer, and esophageal cancer. Since lung cancer is the leading cause of the cancer cell death in the world, the pharmaceutical composition of this embodiment can contribute to treat a large number of lung cancer patients. As to colorectal cancer and colon/rectum cancer, the number of affected individuals is increasing in Japan where the western-style dietary life is settled, and thus the death rate is also increasing. Hence, it is beneficial for patients that the pharmaceutical composition of this embodiment increases the number of options for a therapeutic medicine to colorectal cancer and colon/rectum cancer. As to esophageal cancer, the recurrence rate after a surgery reaches 30 to 50% which is high, and the sensitivity to conventional medicines is low. Therefore, the pharmaceutical composition of this embodiment can improve the treatment results of esophageal cancer.

The pharmaceutical composition of this embodiment may be applied together with at least either one of the PI3K inhibitor and the MAP kinase kinase inhibitor. When applied together with at least either one of the PI3K inhibitor and the MAP kinase kinase inhibitor, the pharmaceutical composition can enhance the oncolytic cytotoxicity in cancer cell lines. Hence, in a cancer therapy, under a current circumstance in which molecular target drugs, such as the PI3K inhibitor and the MAP kinase kinase inhibitor, are introduced, the pharmaceutical composition can enhance the treatment results by the molecular target drugs.

The pharmaceutical composition of this embodiment may be applied together with an anticancer agent. When an anticancer agent that possess different mechanism from that of the pharmaceutical composition is applied together, it can be expected that the antitumor effect is improved.

In addition, the pharmaceutical composition of this embodiment has a robust oncolytic activity even in CDDP, gefitinib, or oxaliplatin-resistant cancer cell lines. Hence, it becomes possible to provide an effective treatment for so-called refractory cancers that manifest a resistance to that treatments with those anticancer agents.

Furthermore, when containing CVA11 type, the pharmaceutical composition of this embodiment also shows an intensive cytotoxicity in cancer stem cells. It is though that a cancer stem cell is one of cause of cancer recurrence, and the pharmaceutical composition of this embodiment is effective for suppressing a translation of cancer and a recurrence thereof.

Second Embodiment

A second embodiment of the present disclosure will be explained in detail. A pharmaceutical composition of this embodiment contains a nucleic acid derived from CA11 type that infects cancer cells or a nucleic acid derived from EV4 type that infects cancer cells.

The nucleic acid derived from CVA11 type and the nucleic acid derived from EV4 type may be each a virus-derived RNA directly isolated from CVA11 type and EV4 type, a synthesis RNA, or a cDNA corresponding to the base sequence of the isolated virus RNA. In order to isolate a virus RNA, arbitrary techniques can be applied. Example techniques of isolating a virus RNA are a technique based on the use of phenol/chloroform extraction, and a technique of utilizing an isolation based on magnetic beads. In addition, such a nucleic acid may be a virus plasmid or an expression vector with which a nucleic acid to cause a virus is integrated. The expression vector includes a plasmid that can express a DNA coding a necessary virus protein to cause a virion. The expression vector may contain a transcription regulating control sequence functionally coupled with the inserted nucleic acid. The transcription regulating control sequence in this case is, for example, a promoter starting a transcription, and an expression control element that enables ribosome to be coupled with a transcript mRNA.

The example expression vectors applicable are pSV2neo, pEF-PGk.puro, pTk2, an unreplicated adenovirus shuttle vector, and a cytomegalovirus promoter. A cDNA coding a necessary virus protein to cause a virus can be prepared by reverse-transcription of a virus RNA or a fragment thereof.

The pharmaceutical composition of this embodiment may contain, in addition to the nucleic acid derived from CVA11 type that infects cancer cells or the nucleic acid derived from EV4 type that infects cancer cells, a carrier like liposome. The nucleic acid derived from CVA11 type is, for example a nucleic acid having a sequence indicated by a sequence ID 1. In addition, the nucleic acid derived from EV4 type is, for example, a nucleic acid having a sequence indicated by a sequence ID 2.

The pharmaceutical composition of this embodiment can be administered through various techniques. For example, it is preferable to administer the pharmaceutical composition through intratumoral administration, intravenous administration, and intraperitoneal administration in accordance with the kind of cancer. Note that the pharmaceutical composition can be administered orally, or may be administered through a muscle, a skin, a rectum, a vagina, a nose, and the like. In the case of oral administration, the pharmaceutical composition may contain a sweeting agent, a disintegrating agent, a diluent agent, a coating agent, a preserving agent, and the like.

The pharmaceutical composition of this embodiment is administered in such a way that the nucleic acid derived from CVA11 type that infects cancer cells or the nucleic acid derived from EV4 type that infects cancer cells becomes a sufficient amount to cure cancer. The dosage amount is determined in accordance with the body weight of a patient, age, gender, the size of a tumor tissue, and the like. When, for example, the pharmaceutical composition is applied as a liquid medication, it is appropriate if the nucleic acid corresponding to CVA11 type or EV4 type of $1 \times 10^2$ to $1 \times 10^{10}$ plaque-formation unit be contained in the liquid medication of 1 ml. It is preferable that the nuclei acid corresponding to CVA11 type or EV4 type of equal to or greater than $1 \times 10^5$ plaque-formation unit should be contained in the liquid medication of 1 ml. The number of administrations of the pharmaceutical composition may be one or multiple times. In addition, the pharmaceutical composition may be continuously administered as a slow-release formulation.

The pharmaceutical composition of this embodiment may be applied together with at least either one of the PI3K inhibitor and the MAP kinase kinase inhibitor like the first embodiment.

As explained above, the pharmaceutical composition of this embodiment contains the nucleic acid derived from CVA11 type that infects cancer cells or the nucleic acid derived from EV4 type that infects cancer cells.

EXAMPLES

The present disclosure will be explained in more detail with reference to the following examples, but the present disclosure should not be limited to such examples.

First Example

Preparation of EV4 Type (Du Toit)

EV4 type was grown in using RD cells. After EV4 type was left at a constant temperature in an RD cell cultured through multiple generations using Dulbecco's modified Eagle medium (DMEM) for one hour, the culture medium was replaced with a DMEM, and left stationary until a cell degeneration effect was initiated. After the culture medium was eliminated, OPTI-MEM I was added to a culturing petri dish, and a cell was exfoliated and collected using a cell scraper. Note that EV4 type and the RD cell were cultured in an incubator under a condition of 37° C. and 5% $CO_2$. Using liquid nitrogen, freezing of the collected RD cell and melting thereof were repeated three times. Subsequently, it was subjected to a centrifugal separation for 15 minutes at a temperature of 4° C. and at 3000 rpm, and a supernatant was collected. The collected supernatant (virus solution) was stored at a temperature of −80° C.

Calculation of Virus Infectivity Titer (MOI)

An MOI applied below was calculated through the following scheme.

A cell was disseminated in a plate with 96 wells at $5 \times 10^3$ cells/100 μl/well, and maintained for five hours under a condition of 37° C. and 5% $CO_2$. A virus was diluted by 100 times or 1000 times using OPTI-MEM I, and this was applied as a virus liquid concentrate for MOI measurement (the common logarithm of the dilution multiplying factor at this stage will be referred to as L). The virus liquid concentration was diluted step by step and tenfold for each step (the common logarithm of the dilution multiplying factor at this stage will be referred to as d), and a diluted series solution was prepared. Next, the diluted series solution was added to each well by 0.05 ml (the volume of the added diluted series solution will be referred to as v). The number of wells that showed a cell degeneration effect of equal to or greater than 50% after 120 hours was divided by 8 to obtain a value S, and the MOI was calculated through the following formula.

$$\log_{10}(MOI)=L+d(S-0.5)+\log_{10}(1/v)$$

Screening of EV4 Type Through Crystal Violet Technique

A cytotoxicity as a cancer-cell killing effect by EV4 type was evaluated through a crystal violet technique. Each test target cell was disseminated in a plate with 24 wells at a density ($3 \times 10^4$ cells/well) becoming confluent after 72 hours. EV4 type was diluted with OPTI-MEM I so as to accomplish an appropriate infectivity titer (MOI=0.001, 0.01, and 0.1), and a diluted solution of EV4 type was prepared. After substantially six hours, the culture medium was eliminated from the plate, and the diluted solution of EV4 type was added to each well by 20 μl, and the plate was maintained for one hour under a condition of 37° C. and 5% $CO_2$. Next, the diluted solution of EV4 type was eliminated, and each cell culture medium was added to each well by 1 ml, and cultured for 72 hours. After 72 hours, it was gently rinsed with phosphate buffer saline (PBS), and 0.5% glutaraldehyde containing PBS was added to each well by 300 μl, and the well was left stationary at a room temperature for 15 minutes, thereby immobilizing surviving adherent cells. Thereafter, glutaraldehyde containing PBS was eliminated, and the cell was rinsed with PBS, and sterilized water containing 2% ethanol and 0.1% crystal violet was added to each well by 300 μl, and the well was left stationary for 10 minutes at a room temperature, thereby staining the living cells.

Each well of the plate having undergone staining was rinsed twice with sterilized water of 500 μl, and the level of staining was quantified using a scanner. In the quantification, a cell stained with a blue-purple color was processed as a living cell. The survival rate (%) of the cells was calculated from the area of living cells quantified using Image Gauge Software Ver. 4.1. The cytotoxicity was evaluated based on the killed cells, that is, a value obtained by subtracting the survival rate from 100%.

The test target cells in this case were small cell lung cancer (SBC-5, SBC-3), non-small cell lung cancer (H1299, H460, LK87, A549), lung squamous cell carcinoma (QG95), colorectal cancer (DLD-1, SW620, HT29, Lovo, Caco-2), pancreatic cancer (BxPC3, Panc-1, MiaPaca-2, Aspc-1), malignant mesothelioma (MSTO, H2052, H2452), esophageal cancer/epidermoid cancer (T.Tn, TE6, TE8), oral squamous cell carcinoma (HSC3, HSC4), hypopharynx cancer (FaDu), and human normal dermis horny cell (HaCaT).

Quantification of Expression Level of Virus Receptors Through Flow Cytometry Technique In order to quantify the expression level of CD49b and that of CD55 in the test target cell surface, each cell reacted with a fluorescently labeled antibody was analyzed through a flow cytometry technique. The cultured cell was collected, and was suspended in PBS so as to be $2\times10^6$ cells/ml. The obtained cell suspending solution was dividedly added to respective wells of the plate with 96 wells by 100 µl ($2\times10^5$ cells/well). It was subjected to a centrifugal separation for 5 minutes at 4° C. and 2000 rpm, and 1% bovine serum albumin (BSA) containing PBS containing fluorescein-isothiocyanate (FITC) labeled anti-human CD49b antibody, or phycoerythin (PE) labeled anti-DAF (CD55) antibody was added to pellets by 100 µl for each pellet. The plate was left stationary for one hour in ices to let the antibody reacted. The control cell was labeled using an isotype IgG antibody.

After labeling with the antibody, it was rinsed twice by 1% BSA containing PBS, and as to the rinsed cells, the expression levels of CD49b and CD55 were quantified as a ratio (%) relative to the expression level in the control cells using FACS Calibur (Registered Trademark). FlowJo Software Ver. 7.6 was utilized for data analysis.

(Results)

Table 1 shows the cytotoxicity of EV4 type to various cancer cell lines, the expression level of CD49b and that of CD55. Regarding the cytotoxicity to cancer cells, when the cytotoxicity evaluated through the crystal violet technique was equal to or greater than 66%, it was indicated as "3+", when equal to or greater than 33% but less than 66%, it was indicated as "2+", when higher than 0% but less than 33%, it was indicated as "+", and when 0%, it was indicated as "−". As a result, a high cytotoxicity was observed in some cell lines of small cell lung cancer, non-small cell lung cancer, colorectal cancer, and pancreatic cancer. In addition, in all cell lines of esophageal cancer/epidermoid cancer, a high cytotoxicity was observed although MOI=0.001 that was quite low. All cell lines of esophageal cancer/epidermoid cancer showed a high expression of CD49b and that of CD55 that were equal to or greater than 90%. Based on those results, it is indicated that EV4 type infects cancer cells with a virus receptors that is CD49b and CD55.

As to human normal dermis horny cell (HaCaT), the cytotoxicity was 0% in all MOI.

TABLE 1

| | | MOI | | | CD49b | CD55 |
|---|---|---|---|---|---|---|
| | Cell line | 0.001 | 0.01 | 0.1 | (%) | (%) |
| Small cell lung cancer | SBC-5 | 3+ | 3+ | 3+ | — | — |
| | SBC-3 | − | − | − | — | — |
| Non-small cell lung cancer | H1299 | 3+ | 3+ | 3+ | — | — |
| | H460 | − | − | − | 14.9 | 100 |
| | LK87 | 2+ | 3+ | 3+ | — | — |
| | A549 | 2+ | 3+ | 3+ | 83.9 | 100 |
| Lung squamous cell carcinoma | QG95 | − | − | − | — | — |
| Colorectal cancer | DLD-1 | − | − | − | 98.6 | 99 |
| | SW620 | − | − | − | 41.2 | 99 |
| | HT29 | 3+ | 3+ | 3+ | 98.5 | 98.8 |
| | LoVo | − | − | − | — | — |
| | Caco-2 | − | 2+ | − | 76.4 | 100 |
| Pancreatic cancer | BxPC3 | − | − | − | 91.2 | 94.7 |
| | Panc-1 | − | − | − | 87.8 | 98 |
| | MiaPaCa-2 | 3+ | 3+ | 3+ | 56.6 | 80 |
| | Aspc-1 | 3+ | 3+ | 3+ | 89 | 100 |

TABLE 1-continued

| | | MOI | | | CD49b | CD55 |
|---|---|---|---|---|---|---|
| | Cell line | 0.001 | 0.01 | 0.1 | (%) | (%) |
| Malignant mesothelioma | MSTO | − | − | − | 94 | 99 |
| | H2052 | − | − | − | — | — |
| | H2452 | − | − | − | — | — |
| Esophageal cancer/ epidermoid cancer | T.Tn | + | 2+ | 3+ | 99 | 99 |
| | TE6 | 2+ | 3+ | 2+ | 96 | 98 |
| | TE8 | 2+ | 3+ | 2+ | 93 | 99 |
| Oral squamous cell carcinoma | HSC3 | − | − | − | — | — |
| | HSC4 | − | − | − | 99 | 99 |
| Hypopharynx cancer | FaDu | − | − | − | 68.8 | 79.6 |

FIG. 1 shows a microscope image of cell lines (T.Tn, TE8, TE6) of esophageal cancer/epidermoid cancer having undergone crystal violet staining. For each of T.Tn that was an anaplastic cell line, TE8 that was a cell line of moderately differentiated epidermoid cancer, and TE6 that was a cell line of well-differentiated epidermoid cancer, EV4 type showed a cytotoxicity in an MOI-dependent manner. Since EV4 type showed the cytotoxicity to T.Tn that was poor-prognosis (refractory), it is indicated that the pharmaceutical composition containing EV4 type is effective for the therapy of refractory esophageal cancer. In addition, EV4 type did not show a cytotoxicity to a human normal cell, but showed the cytotoxicity specific to cancer cells.

Second Example

Effects of Various Inhibitors to Cytotoxicity of EV4 Type (1)

The inhibitors tested to check the effects to the cytotoxicity of EV4 type were Z-VADfmk (R&D System Corporation) as a pan-caspase inhibitor, LY294002 (Santa Cruz Biotechnology Corporation) as a PI3K inhibitor, PD0325901 (Wako Corporation) as an MEK inhibitor, and bpV (Merck Corporation) as a PTEN inhibitor.

T.Tn was disseminated in a plate with 96 wells at $1\times10^4$ cells/well, and the plate was left stationary under a condition of 37° C. and 5% $CO_2$. The culture medium in the well was replaced with a culture medium added with each inhibitor so as to be 100 µl/well. As to the concentrations of the respective inhibitors, 100 µM for Z-VADfmk, 25 µM for LY294002, 0.1 µM for PD0325901, and 1.0 µM for bpV. After the culture medium was replaced, the plate was left stationary under a condition of 37° C. and 5% $CO_2$ for one hour. After the culture medium was eliminated, 100 µl of the diluted solution of EV4 type diluted with OPTI-MEM I so as to make EV4 type to be MOI=0.1 was added to each well, and was left stationary under a condition of 37° C. and 5% $CO_2$ for one hour. Next, the diluted solution of EV4 type was eliminated, and the RPMI culture media containing the respective inhibitors were added to respective wells, and were co-cultured. Four days after the start of co-culturing, the image of each well was picked up by an optical microscope. Note that the concentration of each inhibitor was set to be a concentration expected not showing a cytotoxicity to T.Tn.

(Results)

Figure 2:
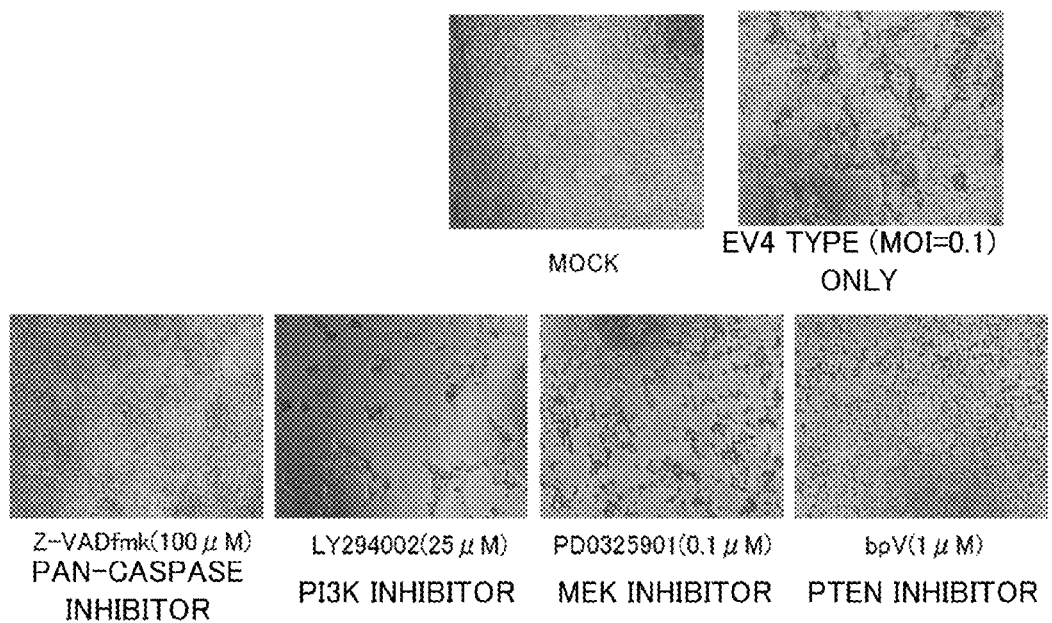
FIG. 2 is a diagram illustrating a cytotoxicity of EV4 type against a cell line of esophageal cancer under the presence of each inhibitor.

FIG. 2 is a diagram illustrating, with microscope images, effects to the cytotoxicity four days after infection when only EV4 type (DMSO, MOI=0.1) was administered to T.Tn, when EV4 type and a pan-caspase inhibitor (Z-VADfmk) as an apoptosis inhibitor were administered, when EV4 type and a PI3K inhibitor (LY294002) were administered, when EV4 type and an MEK inhibitor (PD0325901) were administered, and when EV4 type and a PTEN inhibitor (bpV) known as inhibiting PI3K were administered. The cytotoxicity by EV4 type was reduced by an apotosis inhibitor and a PTEN inhibitor known as inhibiting PI3K. Conversely, the cytotoxicity by EV4 type was enhanced by a PI3K inhibitor and an MEK inhibitor.

Therefore, it is indicated that caspase-dependent apotosis and PI3K/Akt, MEK/ERK cell growth signal transducing system is relevant to the cytotoxicity by EV4 type (growth mechanism in an esophageal cancer cell by EV4). Hence, it is potently indicated that the pharmaceutical composition containing EV4 type enhances the antitumor effect when applied together with PI3K (Akt) that is a new molecular target drug recently utilized in clinical tests for solid cancer therapy, or an MEK inhibitor (MAP kinase kinase inhibitor).

Third Example

Effects of Various Inhibitors to Cytotoxicity of EV4 Type (2)

An effect of an MEK inhibitor PD0325901 to the cytotoxicity of EV4 type was quantitatively examined.

TE8 cells was disseminated in a plate with 96 wells at $1 \times 10^4$ cells/well, and the plate was left stationary for six hours under a condition of 37° C. and 5% $CO_2$. The culture medium in the well was replaced with a culture medium containing a DMSO solution of PD0325901 of 50-nM. After the culture medium was replaced, the plate was left stationary for one hour under a condition of 37° C. and 5% $CO_2$. After the culture medium was eliminated, 100 µl of EV4 type diluted solution diluted with OPTI-MEM I so as to have MOI=1.0 was added to each well, and the plate was left stationary for one hour under a condition of 37° C. and 5% $CO_2$. For a control, a diluted solution of 100 µl containing no EV4 type was added. Next, the diluted solution was eliminated, and the culture media containing PD0325901 were added to respective wells, and were co-cultured. 48 hours after the start of co-culturing, living cells were quantitated using a Celltilter-Glo (Registered Trademark) kit of Promega corporation.

(Results)

Figure 3:
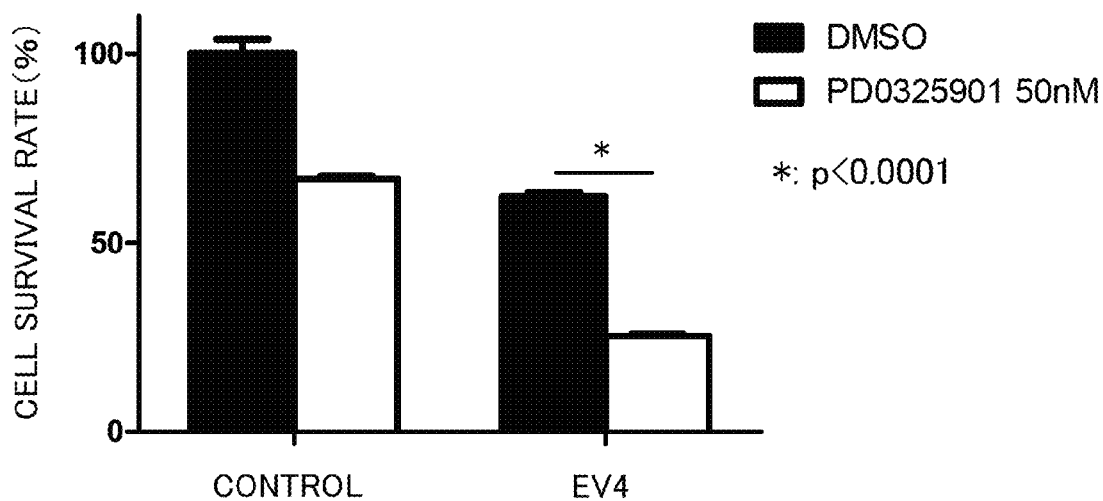
FIG. 3 is a diagram illustrating a cytotoxicity of EV4 type against a cell line of esophageal cancer under the presence of an MEK inhibitor.

FIG. 3 indicates a cell survival rate of the control and that of TE8 infected with EV4 type. When PD0325901 was activated, the cytotoxicity of EV4 type in TE8 cells was significantly enhanced.

As a result, it is indicated that the pharmaceutical composition containing EV4 type enhances the antitumor effect when applied together with an MEK inhibitor.

Fourth Example

Evaluation on In Vivo Antitumor Effect of EV4 Type (1)

A tumor refraction performance by the cytotoxicity of EV4 type to cancer cells confirmed thorough the first example was examined using a tumor bearing mouse by a cell line TE8 cells of human esophageal cancer/epidermoid cancer. TE8 was rinsed with PBS, and was suspended in OPTI-MEM I so as to be $1.0 \times 10^7$ cells/ml. The suspending solution containing TE8 cells was applied to the right abdomen of a mouse through hypodermic injection using 27 G needle 100 µl by 100 µl. The mice were sorted at random for a non-administered group and three EV4 type administered groups. The major axis and minor axis of a tumor were measured using a caliper. When the tumor major axis became substantially 4 mm and it was confirmed that the tumor was settled in the mouse, an EV4 type solution suspended in OPTI-MEM I of 50 µl was once administered in the tumor. The infectivity titers of EV4 type administered to the respective EV4 type administered groups were $1.0 \times 10^5$, $1.0 \times 10^6$, and $1.0 \times 10^7$ $TCID_{50}$. $TCID_{50}$ was evaluated five days after the virus infection using an RD cell that was a cell of a human strained muscle sarcoma. For the non-administered group, OPTI-MEM I containing no EV4 type was administered to the right abdomen at the same dosage as those of the EV4 type administered groups. Four days after the administration of EV4 type, the tumor volume and the body weight of each EV4 type administered group were measured. Note that the tumor volume was calculated by major axis×minor axis×minor axis×0.5.

(Results)

Figure 4:
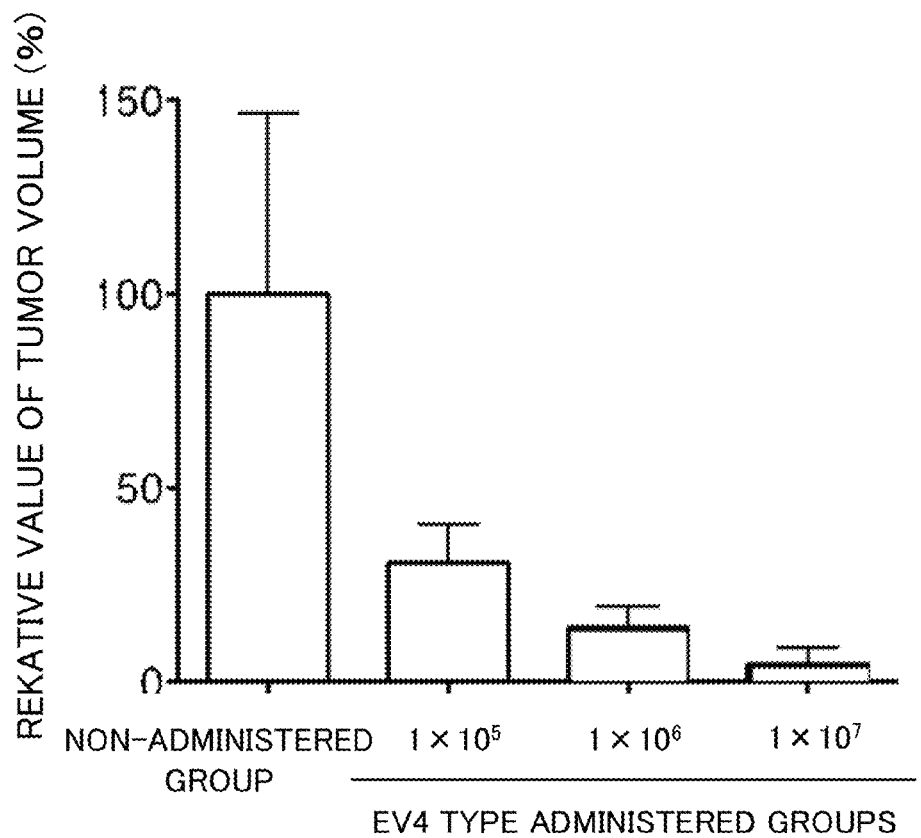
FIG. 4 is a diagram illustrating an effect of EV4 type against volumes of tumors formed in human esophageal cancer xenografts-bearing mice.
Figure 5:
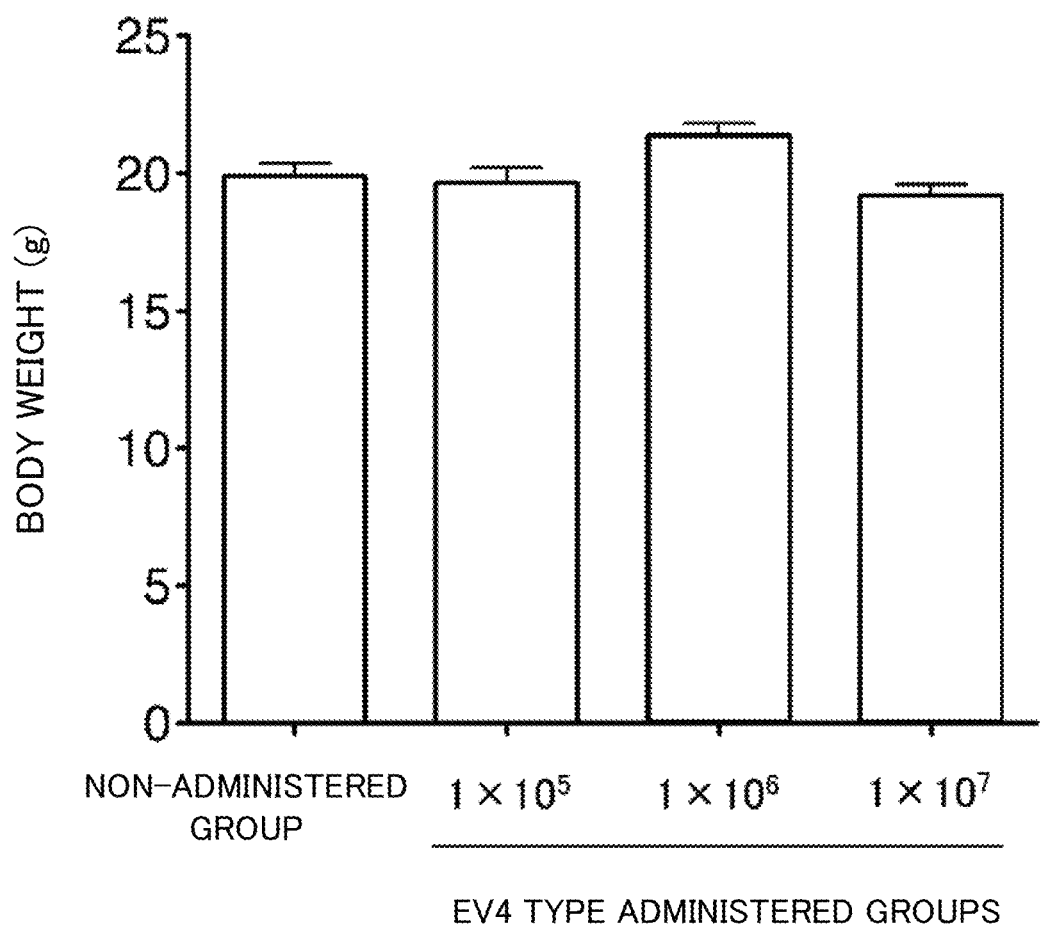
FIG. 5 is a diagram illustrating body weight of the human esophageal cancer xenografts-bearing mice in FIG. 4.

FIG. 4 illustrates a relative value of the tumor volume of each EV4 type administered group relative to the tumor volume of the non-administered group. According to the mice administered with EV4 type, in comparison with the non-administered group, the increase of the tumor volume was significantly suppressed in an EV4 type-administration dependent manner. In addition, FIG. 5 illustrates a body weight of the non-administered group and that of each EV4 type administered group. As a result, a significant body weight reduction was not observed in the EV4 type administered group. Since the body weight reduction at this stage indicates an adverse event, observation of no body weight reduction indicates that there is no apparent adverse event by the administration of EV4 type. This is different from the enterovirus CV A21 type having a lethal and serious adverse event admitted, confirming the safeness of EV4 type.

Fifth Example

Evaluation on In Vivo Antitumor Effect of EV4 Type (2)

A tumor refraction performance by the cytotoxicity of EV4 type was further examined using mice bearing TE8 xenografts. TE8 cells was rinsed with PBS, and was suspended in OPTI-MEM I. TE8 cells was applied to the right abdomen of a nude mouse through hypodermic injection using 27 G needle at $2.0 \times 10^6$ cells/administration. When it was confirmed that the tumor major axis measured using a caliper became equal to or greater than 4 mm (0th day), an EV4 type solution suspended in OPTI-MEM I of 50 µl was administered in the tumor once per a day, and total of 10 times so as to be $1 \times 10^7$ $TCID_{50}$/administration. For a control, OPTI-MEM I was administered at the same dosage. In order to examine the dependency of the tumor refraction performance relative to the infectivity titer, a $5 \times 10^7$ $TCID_{50}$/ administered group was added to the similar test. The evaluation items were the tumor volume and the body weight like the fourth example. In addition, the presence/absence of the adverse effect was observed.

(Results)

Figure 6:
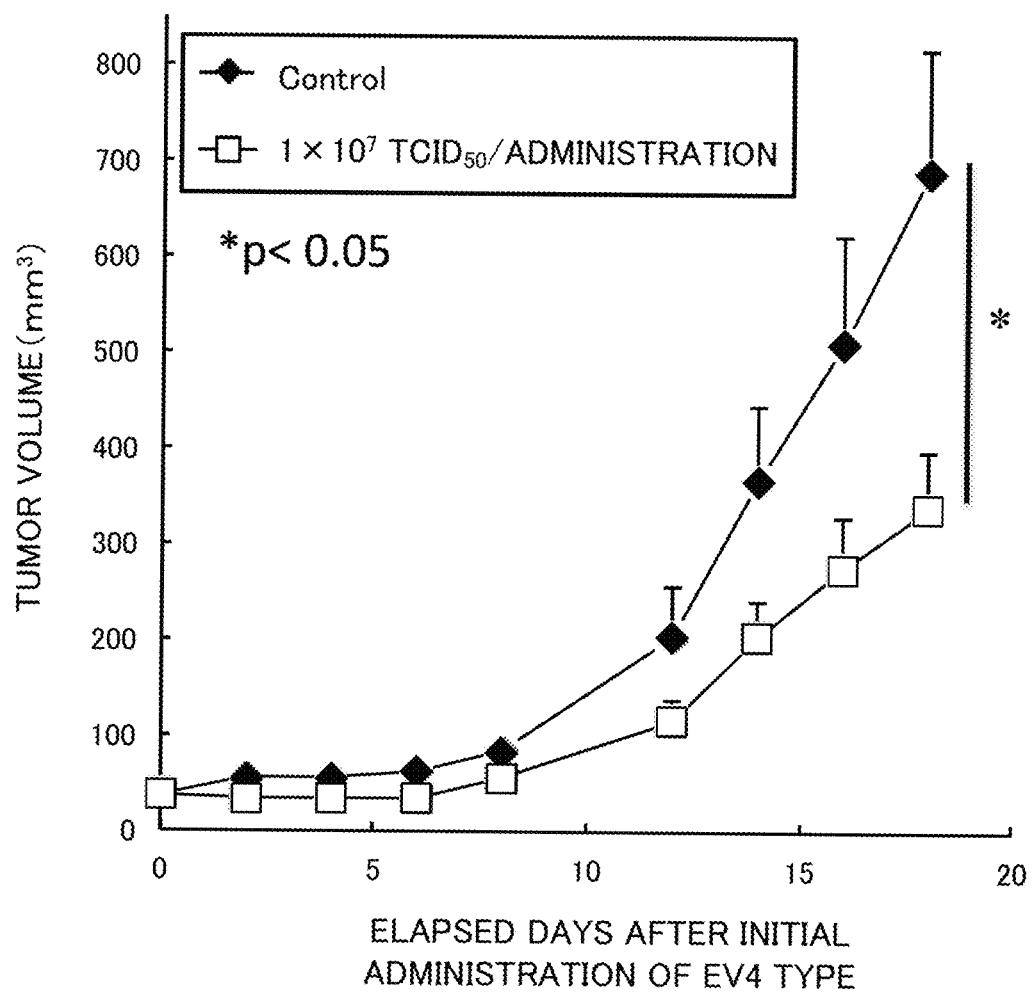
FIG. 6 is a (first) diagram illustrating a change with time in the tumor volume of a human esophageal cancer xenografts-bearing mice administered with EV4 type.
Figure 7:
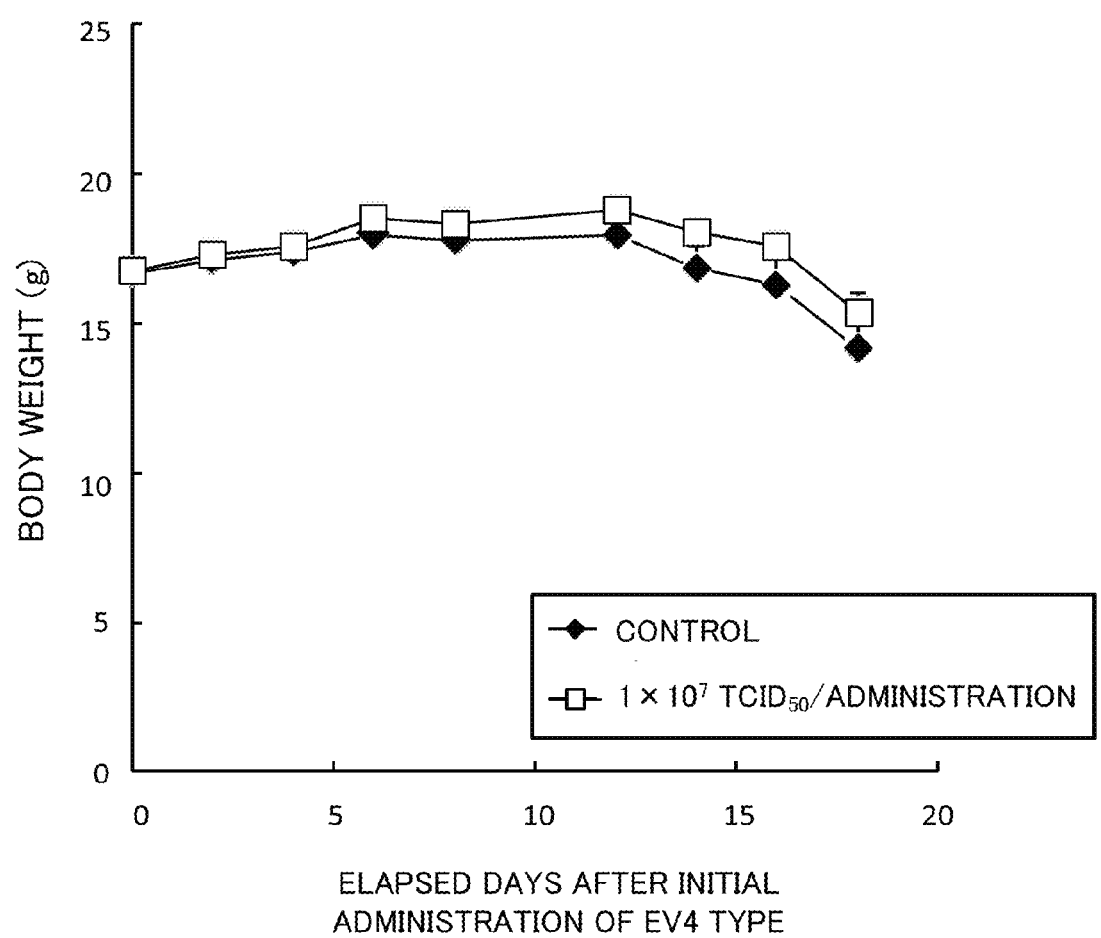
FIG. 7 is a diagram illustrating a change with time in the body weight of the human esophageal cancer xenografts-bearing mice administered with EV4 type in FIG. 6.

FIG. 6 illustrates a change with time in the tumor volume. In comparison with a control, according to the mouse administered with EV4 type, a suppression of the increase of the tumor volume was observed. The tumor volume of the mouse administered with EV4 type became only substantially 50% of the control at 18th day after the first administration of EV4 type, and thus a significant tumor retraction performance was observed. A change with time in the body weight of the mouse is illustrated in FIG. 7. The body weight was maintained like the control, and no serious adverse event was observed.

Figure 8:
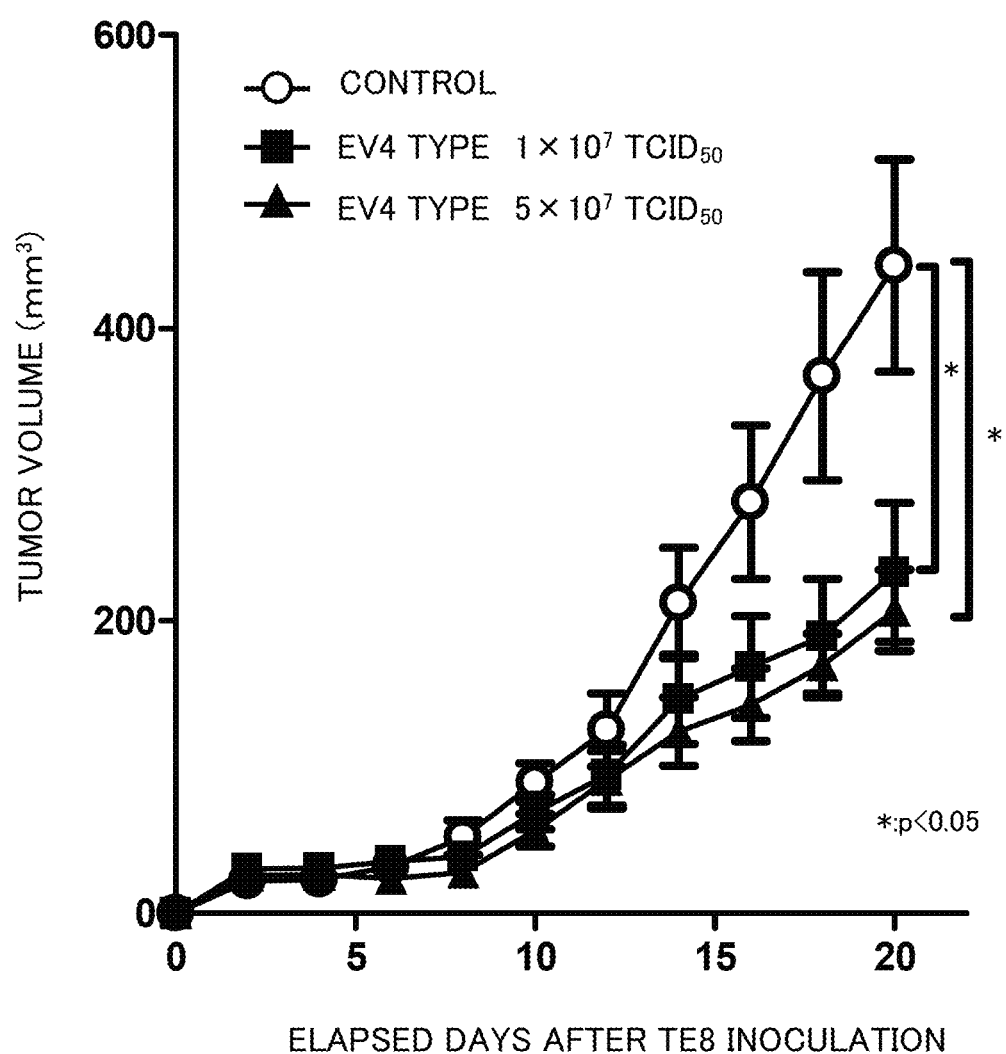
FIG. 8 is a (second) diagram illustrating a change with time in the tumor volume of human esophageal cancer xenografts-bearing mice administered with EV4 type.
Figure 9:
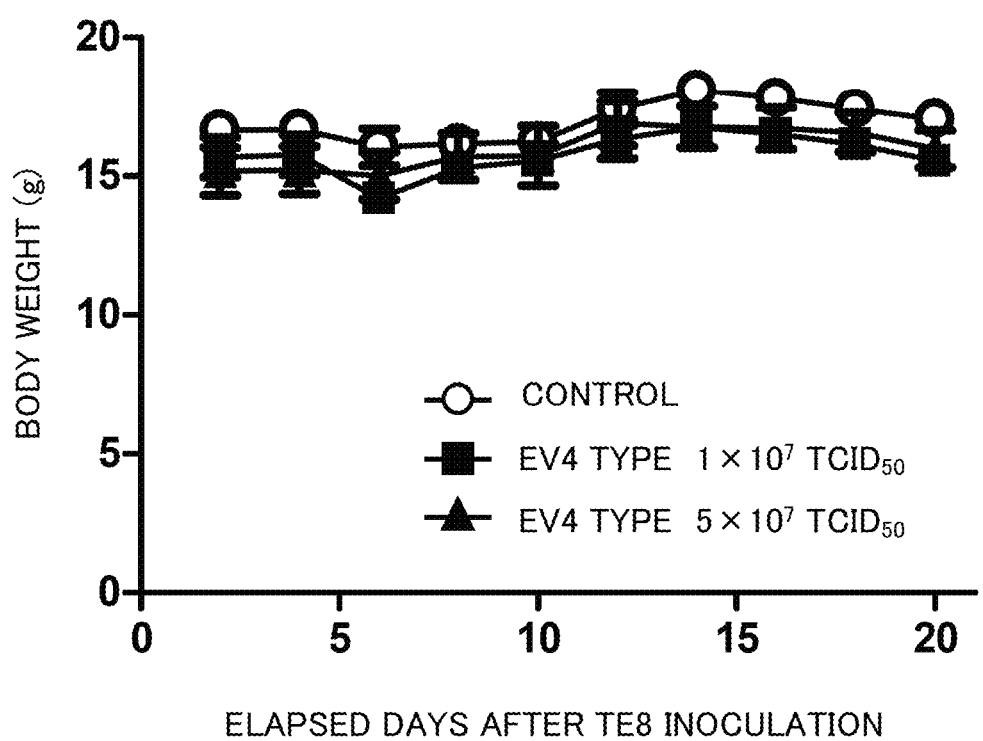
FIG. 9 is a diagram illustrating a change with time in the body weight of the human esophageal cancer xenografts-bearing mice in FIG. 8.

FIG. 8 illustrates a change with time in the tumor volume when EV4 type of two kinds of infectivity titers was administered. The EV4 type administered group showed an infectivity titer dependency for the suppression of the increase of the tumor volume by EV4 type. FIG. 9 illustrates a change with time in the body weight of the mouse in this test. Even if EV4 with enhanced infectivity titer was administered, the body weight was maintained like the control, and thus no serious adverse event was observed.

Based on the above-explained facts, it is indicated that EV4 type ensures a high safeness for a relatively long time even if administered multiple times, and accomplishes the antitumor effect.

Sixth Example

Evaluation on In Vivo Antitumor Effect of EV4 Type to CDDP Resistant Tumor

The tumor refraction performance of EV4 type to a TE8 bearing nude mouse indicating a resistivity against CDDP (also called cisplatin) utilized in chemotherapies for esophageal cancer was examined. A nude mouse was inoculated with TE8 like the fifth example (0th day), and when it was confirmed that the tumor major axis became equal to or greater than 4 mm, CDDP dissolved in a normal saline solution was administered in an abdominal cavity at 125 μg/administration (second day). Note that for a non-treated group, the same amount of normal saline solution was administered. Eight days after the inoculation of TE8, furthermore, an EV4 type solution suspended in OPTI-MEM I of 50 μl was administered in the tumor once per a day and at a total of five times and at $1\times10^7$ $TCID_{50}$/administration or $5\times10^7$ $TCID_{50}$/administration. For the non-treated group and the CDDP administered group, the same amount of OPTI-MEM I was administered. The evaluation items were the tumor volume and the body weight like the fourth example.

(Results)

Figure 10:
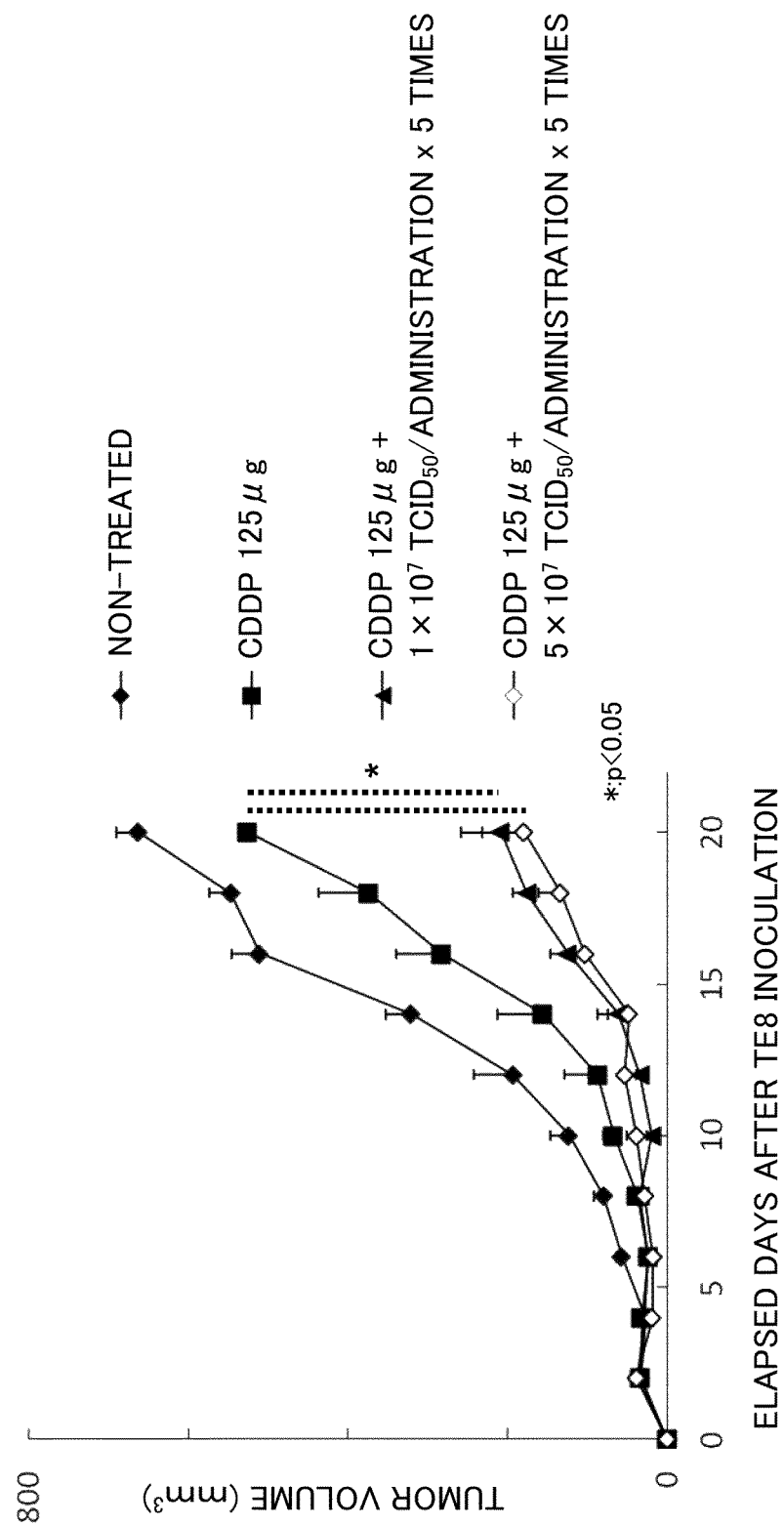
FIG. 10 is a diagram illustrating a change with time in the tumor volume of human esophageal cancer xenografts-bearing mice administered with EV4 type in combination with CDDP.

FIG. 10 illustrates a change with time in the tumor volume. The CDDP administered group showed a suppression of the increase of the tumor volume for eight days, but the increase of the tumor volume was observed thereafter. As to the TE8 tumor bearing nude mouse indicating a resistivity against CDDP as explained above, the mice administered with EV4 type of $1\times10^7$ $TCID_{50}$ and $5\times10^7$ $TCID_{50}$ both showed a significant suppression of the increase of the tumor volume, and indicated an antitumor effect to the CDDP resistant tumor in comparison with the control and the CDDP administered group, respectively.

Figure 11:
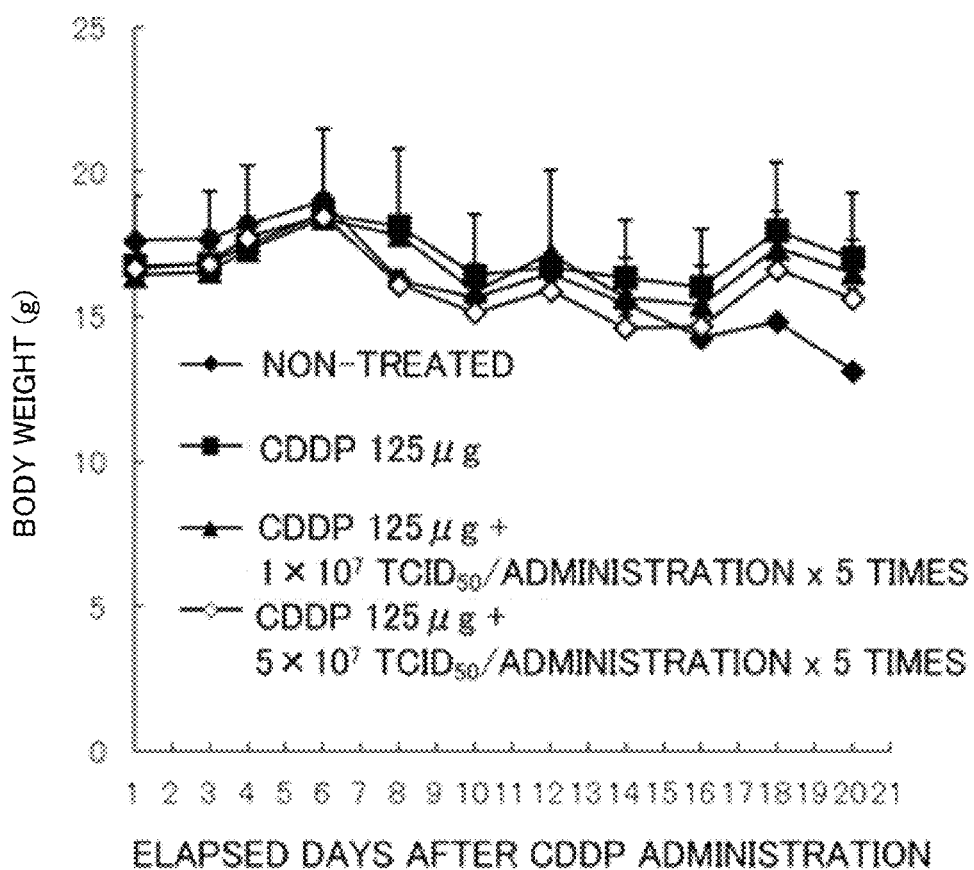
FIG. 11 is a diagram illustrating a change with time in the body weight of the human esophageal cancer xenografts-bearing mice.

FIG. 11 illustrates a change with time in the body weight of a TE8 tumor bearing nude mouse. Although EV4 was administered, the body weight was maintained, and no serious adverse event was observed.

Based on the above-explained facts, it is indicated that EV4 type accomplishes an antitumor effect to an anticancer-agent resistant tumor with a high safeness. In addition, it is indicated that EV4 type accomplishes an intensive antitumor effect to an anticancer-agent resistant tumor when applied together with an anticancer agent like CDDP.

Seventh Example

Screening of CVA11 Type Through Crystal Violet Technique (1)

Like the first example, the cytotoxicity of CVA11 type as a cancer-cell killing effect was evaluated. The test target cells were small cell lung cancer (SBC-5, SBC-3), non-small cell lung cancer (H1299, H460, LK87, and A549), lung squamous cell carcinoma (QG95), colorectal cancer (DLD-1, SW620, Lovo, and Caco-2), malignant mesothelioma (MSTO, H2052, H2452, and H28), esophageal cancer/epidermoid cancer (T.Tn, TE6, TE8), oral squamous cell carcinoma (HSC3, HSC4), hypopharynx cancer (FaDu), throat cancer (Hep2) and human-B-lymphocyte tumor (Daudi).

Quantification of Virus Receptors Through Flow Cytometry Technique

In order to quantify the expression level of CD54 and that of DC55 on the surfaces of the above-explained test target cells, each cell reacted with a fluorescently labeled antibody was analyzed through the flow cytometry technique like the first example. Allophycocyanin (APC) labeled anti-human CAM-1 (CD54) antibody was utilized to detect CD54. Note that Daudi was excluded from the quantification of the virus receptors.

(Results)

Table 2 shows the cytotoxicity of CVA11 type and respective expression levels of CD54 and CD55. For non-small lung cancer cell lines H1299 and H460, an intensive cytotoxicity was confirmed when MOI=equal to or greater than 0.001. For A549, an intensive cytotoxicity was confirmed when MOI=0.1. Conversely, for all cell lines of colorectal cancer, an intensive cytotoxicity was confirmed when MOI=0.1, and for SW620, an intensive cytotoxicity was confirmed although MOI=0.001. In addition, for LoVo, an intensive cytotoxicity was confirmed although MOI=0.01. For cell lines TE6 and TE8 of esophageal cancer/epidermoid cancer, an intensive cytotoxicity was confirmed when MOI=0.01. Still further, an intensive cytotoxicity was also confirmed in the cases of cell line SBC-3 of small cell lung cancer, cell lines MSTO and H2052 of malignant mesothelioma, cell line FaDu of hypopharynx cancer, and cell line Daudi of human-B-lymphocyte tumor.

Yet further, for cells with a low CD54 expression (SBC-5, LK87, QG95, H28, and Hep2), no cytotoxicity was confirmed, and it is indicated that ICAM-1 is one of the virus receptors for CVA11 type.

TABLE 2

|  |  | MOI | | | CD54 | CD55 |
|---|---|---|---|---|---|---|
|  | Cell line | 0.001 | 0.01 | 0.1 | (%) | (%) |
| Small cell lung cancer | SBC-5 | – | – | – | 0.9 | 99.6 |
|  | SBC-3 | + | 2+ | 3+ | 92.1 | 76 |
| Non-small cell lung cancer | H1299 | 3+ | 3+ | 3+ | 78.1 | 98.4 |
|  | H460 | 2+ | 3+ | 3+ | 21.3 | 99.8 |
|  | LK87 | – | – | – | 38.4 | 97.8 |
|  | A549 | – | 1+ | 3+ | 28.1 | 100 |
| Lung squamous cell carcinoma | QG95 | – | – | – | 13.4 | 99.3 |
| Colorectal cancer | DLD-1 | – | + | 3+ | 98.5 | 99.6 |
|  | SW620 | 3+ | 3+ | 3+ | 96.7 | 99 |
|  | LoVo | + | 2+ | 3+ | 9.5 | 95.8 |
|  | Caco-2 | – | + | 3+ | 99.8 | 99.8 |

TABLE 2-continued

|  |  | MOI | | | CD54 (%) | CD55 (%) |
| --- | --- | --- | --- | --- | --- | --- |
|  | Cell line | 0.001 | 0.01 | 0.1 | | |
| Malignant mesothelioma | MSTO | − | 2+ | 3+ | 96.7 | 97.5 |
| | H2052 | + | 3+ | 3+ | 65.9 | 88.5 |
| | H2452 | − | − | − | 97.7 | 44.6 |
| | H28 | − | − | − | 3.8 | 92 |
| Esophageal cancer/ epidermoid cancer | T.Tn | − | − | − | 95.2 | 99.8 |
| | TE6 | + | 2+ | 3+ | 99.7 | 99.6 |
| | TE8 | 2+ | 3+ | 3+ | 92.1 | 99.4 |
| Oral squamous cell carcinoma | HSC3 | − | − | − | 98.7 | 99.1 |
| | HSC4 | − | − | − | 61 | 97.1 |
| Hypopharynx cancer | FaDu | + | 2+ | 3+ | 95.4 | 99.9 |
| Throat cancer | Hep2 | − | − | − | 12 | 100 |
| Human-B-lymphocyte tumor | Daudi | 2+ | 2+ | 3+ | No Data | No Data |

Figure 12:
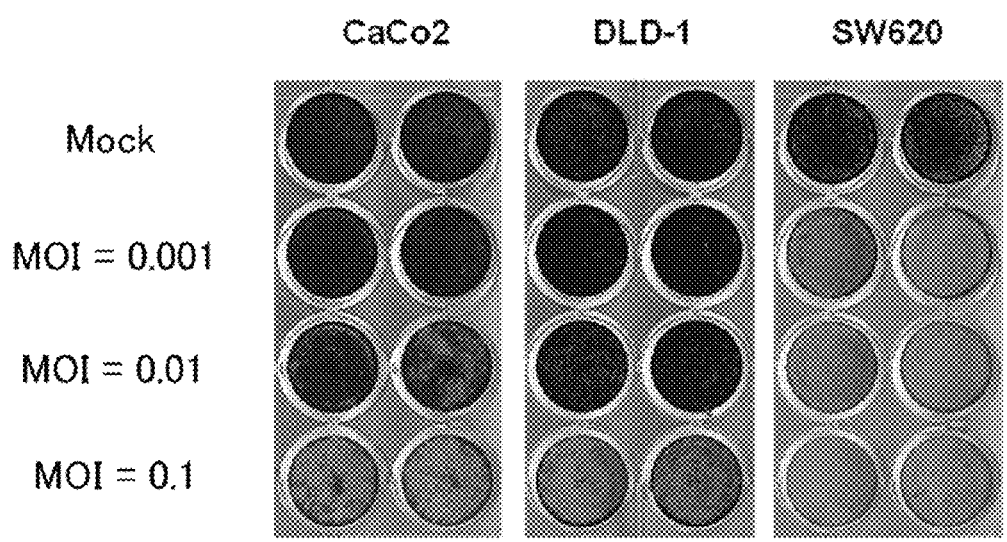
FIG. 12 is a diagram illustrating the cytotoxicity of CVA11 type against colorectal cancer cell lines.

FIG. 12 shows a microscope image of stained cell lines (Caco-2, DLD-1 and SW620) of colorectal cancer. A cytotoxicity was confirmed in all of those cell lines in an MOI-dependent manner. What is notable was that CVA11 type showed the highest cytotoxicity to SW620, with mutation in p53 and k-RAS, known as a standard treatment resistant strain. Based on those results, it is indicated that the pharmaceutical composition containing CVA11 type is effective to treatment-resistant colorectal cancer.

Figure 13:
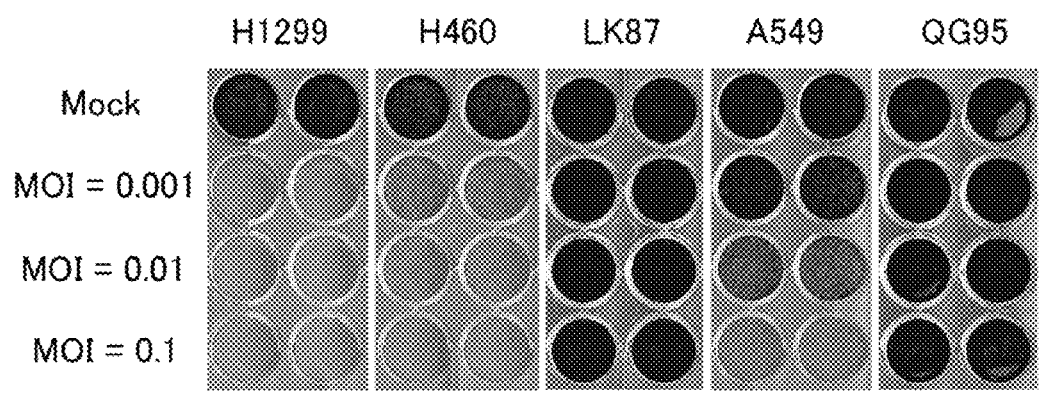
FIG. 13 is a diagram illustrating a cytotoxicity of CVA11 type against non-small cell lung cancer cell lines.

FIG. 13 shows a microscope image of stained non-small cell lung cancer (H1299, H460, LK87 and A549) and that of lung squamous cell carcinoma (QG95). In H1299, H460 and A549 having the cytotoxicity of CVA11 type confirmed, the cytotoxicity was observed in an MOI-dependent manner.

Figure 14:
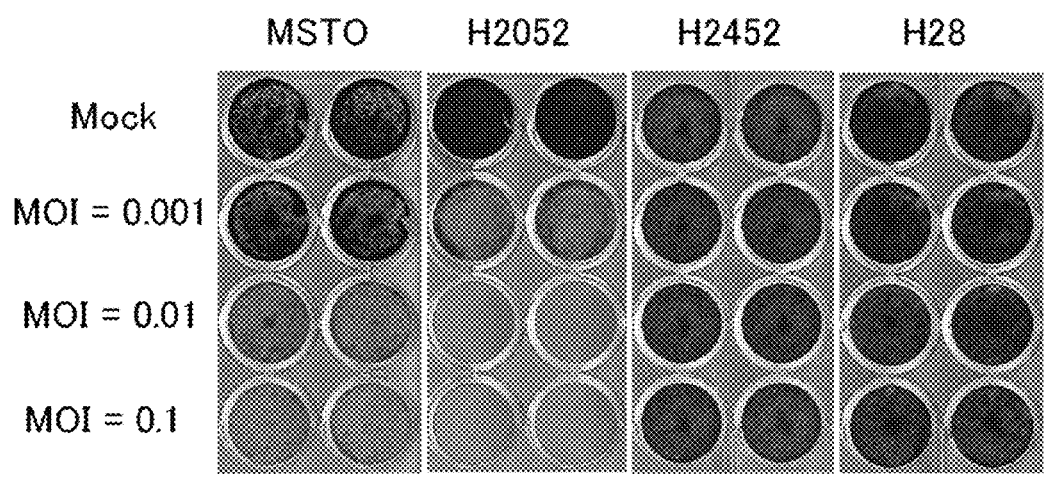
FIG. 14 is a diagram illustrating a cytotoxicity of CVA11 type against malignant mesothelioma cell lines.

FIG. 14 shows a microscope image of stained malignant mesothelioma (MSTO, H2052, H2452, and H28). In MSTO and H2052 having the cytotoxicity of CVA11 type confirmed, the cytotoxicity was observed in an MOI-dependent manner.

Eighth Example

Examination of Infection Mechanism of CVA11 Type (Effect of ICAM-1 Neutralization Antibody to Cytotoxicity of CVA11 Type to Bowl Cancer Cell Line)

Colorectal cancer cell lines (DLD-1 and SW620) were disseminated in a plate with 48 wells at $3\times10^4$ cells/well. After the culture medium was eliminated from the plate, an anti-human ICAM-1 antibody (R&D Systems Corporation) solution diluted with the culture medium for each cell was added by 10 µg/ml. After one hour, the culture medium was eliminated and a CVA11 type diluted solution diluted with OPTI-MEM I so as to have MOI=0.001 was added to each well by 100 µl, and maintained for one hour under a condition of 37° C. and 5% $CO_2$. After the infection, the CVA11 type diluted solution was eliminated, and the culture medium for each cell was added to the corresponding well by 1 ml, and was cultured for 12 hours under a condition of 37° C. and 5% $CO_2$. After the culturing, an image of each well was picked up by an optical microscope. The culture media for DL-1 and SW620 were made to be RPMI+10% FBS and DMEM+10% FBS, respectively.

(ICAM-1 Forcible Expression Test)

An RD cell having no ICAM-1 expressed or a cell RD-ICAM-1 into which ICAM-1 genes were introduced through a gene introduction technique using plasmid was disseminated in a plate with 24 wells at $3\times10^4$ cells/well. After cultured for six hours in a DMEM culture medium containing 10% FBS, CVA11 type diluted with OPTI-MEM I was infectively cultured for one hour at each MOI. After three days, the cytotoxicity was evaluated through a crystal violet technique. Note that the expression of ICAM-1 in RD-ICAM-1 was confirmed through a flow cytometry technique.

(Results)

Figure 15:
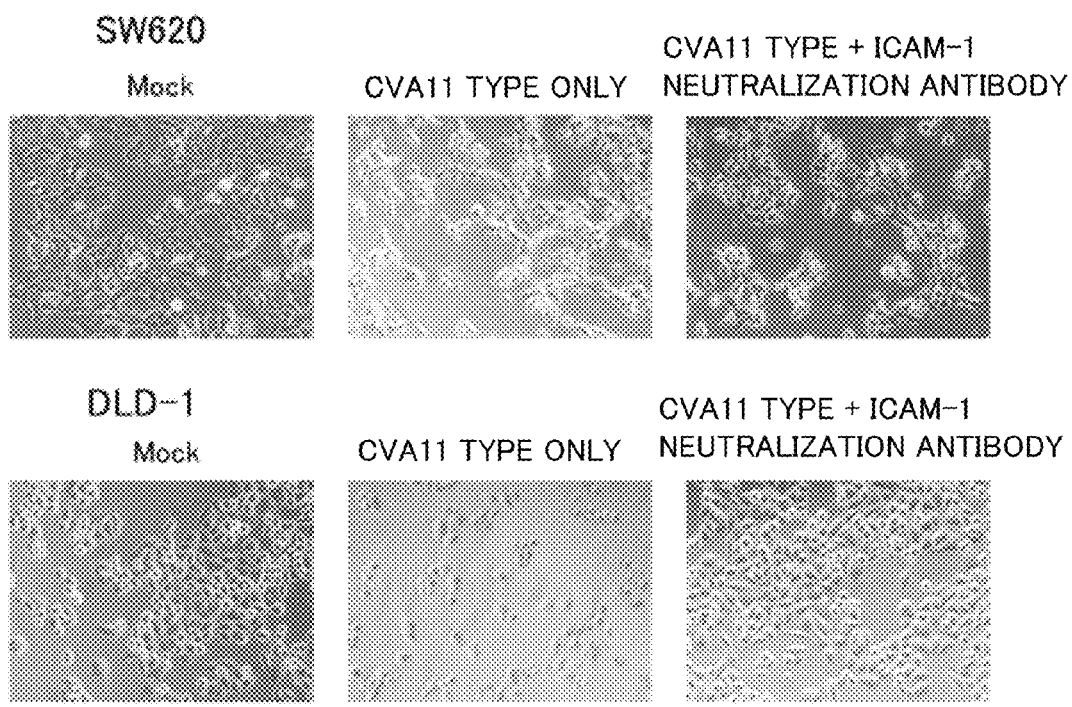
FIG. 15 is a diagram illustrating a cytotoxicity of CVA11 type against human colorectal cancer cell lines in the presence of an anti ICAM-1 neutralization antibody.

FIG. 15 shows optical microscope images of colorectal cancer cell lines (SW620 and DLD-1) picked up after the culturing. In the case of CVA11 type alone, in comparison with a Mock, the number of cells was reduced in both cell lines, and thus a cytotoxicity together with an apparent CPE (Cytopathic Effect) was confirmed. Conversely, under the presence of the anti-ICAM-1 neutralization antibody, the cytotoxicity by CVA11 type disappeared.

Figure 16:
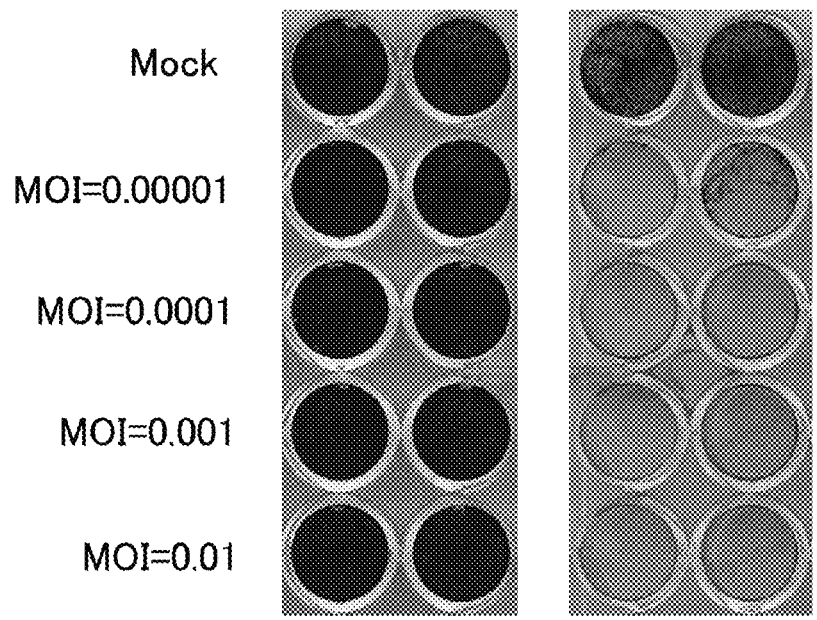
FIG. 16 is a diagram illustrating a cytotoxicity of CVA11 type against parental RD cells and human ICAM-1 overexpressing RD cells.

FIG. 16 shows microscope images of RD cell and RD-ICAM-1 having undergone crystal violet staining in the ICAM-1 forcible expression test. The RD cell having no ICAM-1 expressed did not show the cytotoxicity, but RD-ICAM-1 having ICAM-1 expressed showed an intensive cytotoxicity.

Based on the above-explained facts, it is indicated that ICAM-1 is one of the virus receptors relevant to the infection of CVA11 type.

Therefore, it is proved that ICAM-1 is a virus receptors of CVA11 type, and ICAM-1 is important for the cytotoxicity of CVA11 type. Hence, it is indicated that CVA11 type accomplishes an intensive cytotoxicity to, in particular, cells expressing ICAM-1 among cancer cells.

Ninth Example

Screening of CVA11 Type Through Crystal Violet Technique (2)

The cytotoxicity of CVA11 type as a cancer-cell killing effect was evaluated through a crystal violet technique like the seventh example. In this example, however, each test target cell was disseminated at $2\times10^4$ to $2\times10^5$ cells/well in consideration of the size of each cell and the growth speed thereof. After six hours, the culture medium was eliminated from the plate, and a diluted solution of EV4 type was added to each well by 200 µl, and the plate was maintained under a condition of 37° C. and 5% $CO_2$. Next, the diluted solution of EV4 type was eliminated, the culture medium for each cell was added to each well by 1 ml, and was cultured for 72 hours. The diluted solution of EV4 type was prepared so as to have MOI=0.001, 0.01, 0.1 or 1.0.

The test target cells were, in addition to the cells tested in the seventh example other than HSC3, HSC4, and Daudi, non-small cell lung cancer (H1975, H2009), malignant mesothelioma (MES01, MES04), esophageal cancer/epidermoid cancer (TE1, TE4, TE5, TE9, and KYSE170), colorectal cancer (WiDr, HT29), triple-negative breast cancer (MDA-MB-468, MDA-MB231). breast cancer (MCF7), and cervical cancer (HeLa). Note that A549, H1975 and TE4 were gefitinib primary resistant, gefitinib secondary resistant, and CDDP resistant, respectively.

In addition, in order to check the oxaliplatin resistance of, among the test-target cells, WiDr and HT29, respective cell survival rates of WiDr and HT29 after cultured for 48 hours in culture media containing oxaliplatin of a predetermined concentration were evaluated through an MTS technique.

As is indicated in the seventh example and the eighth example, since ICAM-1 is an receptors of CVA11 type, the expression level of ICMA-1 (CD54) in each cell was quantified like the seventh example.

(Results)

Table 3 shows the cytotoxicity of CVA11 type to respiratory cancer cells and the expression level of CD54. The cytotoxicity was confirmed when at least MOI=0.1 in all cells other than SBC-5, H28 and MES04. CVA11 type showed an intensive cytotoxicity at MOI=0.1 to A549 that was gefitinib primary resistant and H1975 that was gefitinib secondary resistant. In addition, there was a correlation between the cytotoxicity and the expression level of CD54, and in the cells having no cytotoxicity confirmed at MOI=0.1, SBC-5 and H28 had a low expression level of CD54.

TABLE 3

|  |  | MOI | | | CD54 |
|---|---|---|---|---|---|
|  | Cell line | 0.001 | 0.01 | 0.1 | (%) |
| Non-small lung cancer | | | | | |
| (Gefitinib primary resistant) | A549 | — | 1+ | 3+ | 42.0 |
|  | H1299 | 3+ | 3+ | 3+ | 98.7 |
|  | H460 | 2+ | 3+ | 3+ | 60.8 |
|  | LK87 | — | — | 1+ | 38.4 |
| (Gefitinib secondary resistant) | H1975 | — | 1+ | 3+ | — |
|  | H2009 | 3+ | 3+ | 3+ | — |
| Lung squamous cell carcinoma | QG95 | — | — | 1+ | 13.4 |
| Small cell lung cancer | SBC-3 | 1+ | 2+ | 3+ | 92.1 |
|  | SBC-5 | — | — | — | 0.9 |
| Malignant mesothelioma | H2452 | — | 1+ | 2+ | 97.7 |
|  | H2052 | 1+ | 3+ | 3+ | 65.9 |
|  | MSTO | — | 2+ | 3+ | 96.7 |
|  | H28 | — | — | — | 3.9 |
|  | MESO1 | — | 1+ | 2+ | 2.4 |
|  | MESO4 | — | — | — | 94.7 |

Figure 17:
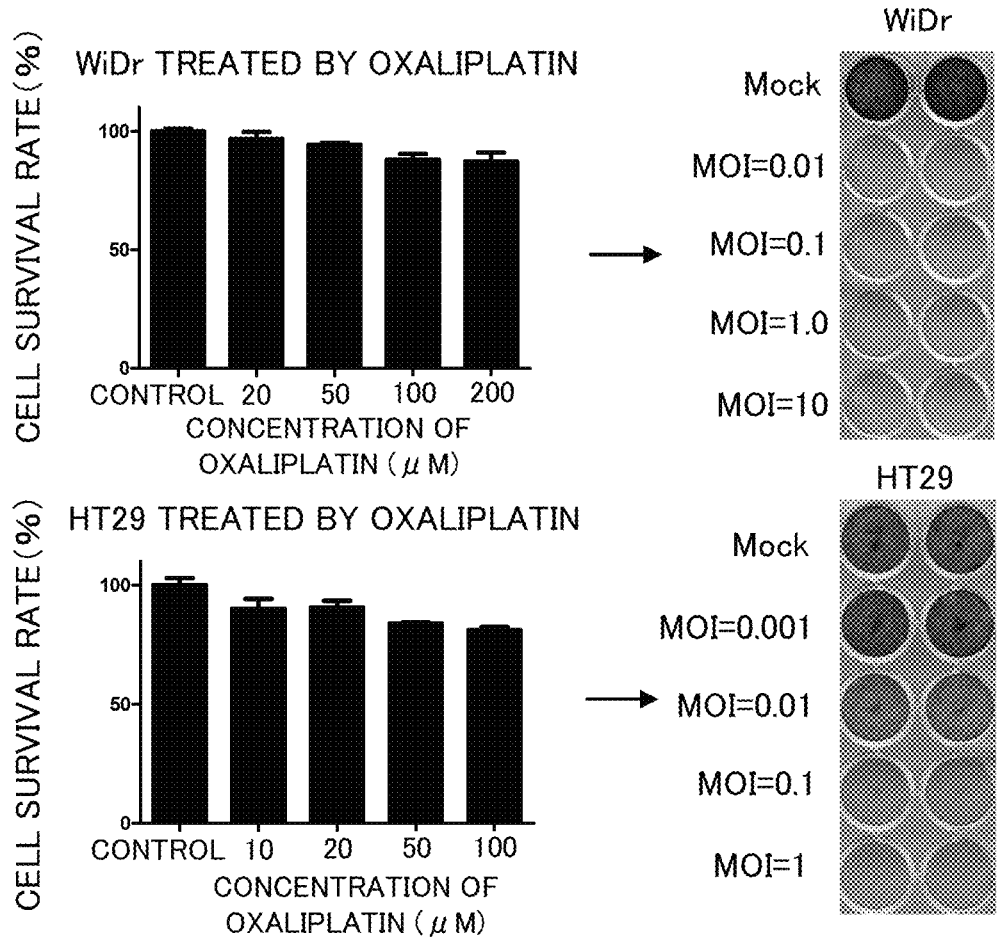
FIG. 17 is a diagram illustrating cell survival rates of WiDr and HT29 cells which were treated with oxaliplatin, and a CVA11 infection-mediated cytotoxicity in WiDr and HT29 cells.

FIG. 17 shows a cell survival rate of WiDr (upper column) and that of HT29 (lower column) treated by oxaliplatin. WiDr and HT29 maintained the similar level of cell survival rate to those of the control group not treated by oxaliplatin although the concentration thereof was high that were 200 μM and 100 μM, respectively. Hence, it is indicated that WiDr and HT29 are oxaliplatin resistant. When WiDr and HT29 were infected with CVA11 type, as is shown in the microscope image of FIG. 17 after crystal violet staining, both WiDr and HT29 showed the cytotoxicity when MOI=equal to or greater than 0.01.

Table 4 shows the cytotoxicity of CVA11 type to head and neck cancer, digestive organ cancer, and breast cancer cells, and the expression level of CD54. All cells other than Hep2 showed an intensive cytotoxicity when at least MOI=0.1. CVA11 type showed an intensive cytotoxicity to TE4 that was a CDDP resistant cell and WiDr and HT29 that were oxaliplatin resistant when at least MOI=0.001 to 0.01. In addition, CVA11 type showed an intensive cytotoxicity to breast cancer cells, in particular, cell lines MDA-MB-468 and MDA-MB-231 of triple negative breast cancer that was a refractory cancer. There was also a correlation between the cytotoxicity and the expression level of CD54, and the expression level of CD54 was low in Hep2 having a cytotoxicity not confirmed when MOI=0.1.

TABLE 4

|  |  | MOI | | | CD54 |
|---|---|---|---|---|---|
|  | Cell line | 0.001 | 0.01 | 0.1 | (%) |
| Esophageal cancer/epidermoid cancer (CDDP resistant) | TE1 | 3+ | 3+ | 3+ |  |
|  | TE4 | 3+ | 3+ | 3+ | 100.0 |
|  | TE5 | 3+ | 3+ | 3+ |  |

TABLE 4-continued

|  |  | MOI | | | CD54 |
|---|---|---|---|---|---|
|  | Cell line | 0.001 | 0.01 | 0.1 | (%) |
|  | TE6 | ± | 2+ | 3+ | 99.7 |
|  | TE8 | 2+ | 3+ | 3+ | 92.1 |
|  | TE9 | — | — | 2+ |  |
|  | T.Tn | — | 1+ | 2+ | 95.2 |
|  | KYSE170 | 2+ | 3+ | 3+ |  |
| Hypopharynx cancer | FaDu | ± | 2+ | 3+ | 95.4 |
| Throat cancer | Hep2 | — | — | — | 12.0 |
| Colorectal cancer | Caco-2 | 3+ | 3+ | 3+ | 99.8 |
|  | LoVo | 1+ | 2+ | 3+ | 9.5 |
|  | DLD-1 | — | 1+ | 3+ | 98.5 |
|  | SW620 | 3+ | 3+ | 3+ | 96.7 |
| (Oxaliplatin resistant) | WiDr | 3+ | 3+ | 3+ | 98.0 |
| (Oxaliplatin resistant) | HT29 | — | 2+ | 3+ | 71.6 |
| Triple negative breast cancer | MDA-MB-468 | 3+ | 3+ | 3+ |  |
|  | MDA-MB-231 | 3+ | 3+ | 3+ |  |
| Breast cancer | MCF7 | 2+ | 3+ |  |  |

Table 5 shows the cytotoxicity of CVA11 type to respiratory cancer when MOI=up to 1.0, and the expression level of CD54. When evaluation was made at MOI=1.0, all cells other than H28 showed the cytotoxicity.

Based on the above-explained results, it is indicated that the pharmaceutical composition containing CVA11 type is effective for the therapy of non-small cell lung cancer, lung squamous cell carcinoma, small cell lung cancer, malignant mesothelioma, esophageal cancer/epidermoid cancer, hypopharynx cancer, colorectal cancer, breast cancer, cervical cancer, and B-lymphocyte tumor, and the like. In addition, it is indicated that the pharmaceutical composition has antitumor effects to gefitinib primary resistant or gefitinib secondary resistant non-small cell lung cancer, CDDP resistant esophageal cancer/epidermoid cancer, oxaliplatin resistant colorectal cancer, and triple negative breast cancer.

TABLE 5

|  |  | MOI | | | CD54 |
|---|---|---|---|---|---|
|  | Cell line | 0.01 | 0.1 | 1.0 | (%) |
| Non-small lung cancer | A549 |  | 1+ | 2+ | 56.0 |
|  | H1299 | 3+ | 3+ | 3+ | 92.6 |
|  | H460 |  | + | 2+ | 37.0 |
|  | LK87 |  | + | 2+ | 7.6 |
|  | H2009 | 3+ | 3+ | 3+ |  |
|  | H1975 | 1+ | 3+ | 3+ |  |
| Lung squamous cell carcinoma | QG95 | — | + | 2+ | 32.2 |
| Malignant mesothelioma | H2452 | — | 1+ | 2+ | 97.7 |
|  | H2052 |  | 2+ | 3+ | 93.9 |
|  | MSTO | — | — | 1+ | 96.7 |
|  | H28 | — | — | — | 3.8 |
|  | MESO-1 | 1+ | 2+ | 3+ | 2.4 |
|  | MESO-4 |  |  | 2+ | 94.7 |
| Cervical cancer | HeLa | 2+ | 3+ | 3+ | 94.1 |

Tenth Example

Detection of Cancer Stem Cell Marker

In order to quantify the expression level of a cancer stem cell marker CD133 on the surfaces of colorectal cancer cells (DLD-1, HT29 and WiDr) among the above-explained test targets, each cell labeled with a PE labeled anti-human CD46 antibody was analyzed through a flow cytometry technique like the first example. To detect CD133, an APC labeled anti-human CD133 antibody was utilized.

(Results)

Figure 18:
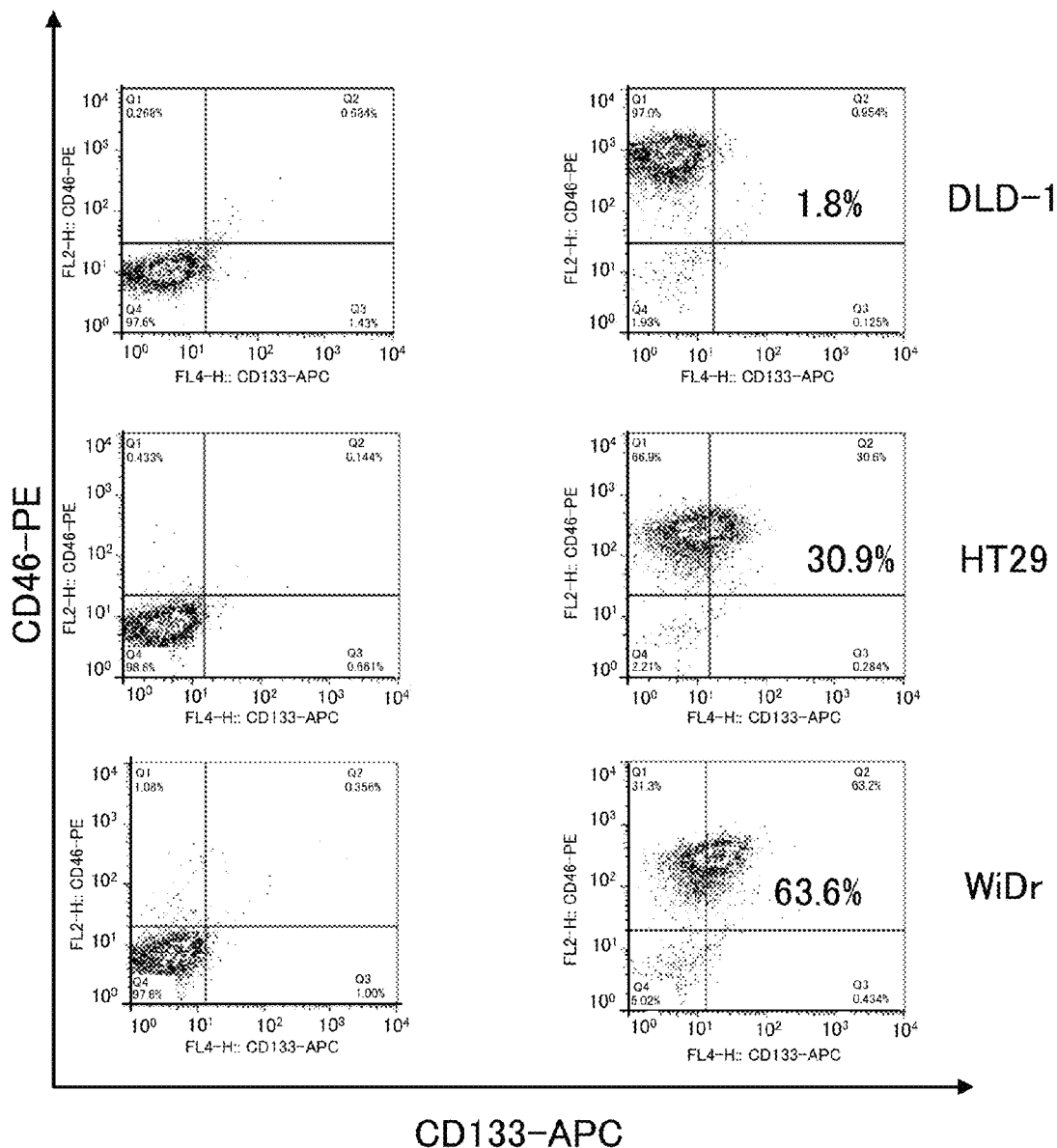
FIG. 18 is a diagram illustrating results of flow cytometry to colorectal cancer cell lines.

FIG. 18 shows an analysis result by the flow cytometry technique. The ratio of the cells expressing CD133 was large in oxaliplatin resistant HT29 and WiDr (30.9% and 63.6%, respectively) relative to DLD-1 (1.8%).

As explained above, it is indicated that, in the oxaliplatin resistant cell line derived from colorectal cancer, the expression level of CD133 is high. In addition, as is indicated in the ninth example, CVA11 type shows an intensive cytotoxicity to oxaliplatin resistant HT29 and WiDr. Therefore, it is indicated that CVA11 type has a cytotoxicity to cancer stem cells.

Eleventh Example

Evaluation on In Vivo Antitumor Effect of CVA11 Type to Oxaliplatin Resistant Tumor An oxaliplatin resistant cancer cell WiDr suspended in 100 μl of PBS was applied to the right abdomen of a nude mouse by $5 \times 10^6$. One day after the application and when it was confirmed that the tumor major axis became equal to or greater than 4 mm, a CVA11 type solution suspended in 50 μl of OPTI-MEM I was administered in the tumor every three days and at a total of four times. The infectivity titer of CVA11 type per an administration was set to be $3 \times 10^6$ $TCID_{50}$. $TCID_{50}$ was evaluated five days after the virus infection using HeLa that was a human cervical cancer cell. The tumor volume was evaluated like the fourth example. For a control, 50 μl of OPTI-MEM I was administered in the tumor.

(Results)

Figure 19:
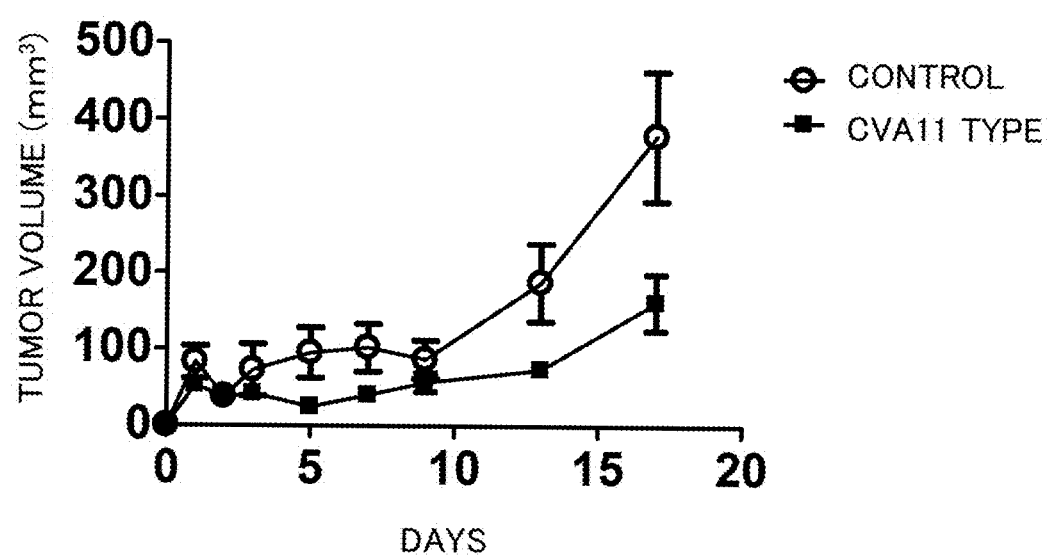
FIG. 19 is a diagram illustrating a change with time in the tumor volume of human colorectal xenografts-bearing mice administered with CVA11 type.

FIG. 19 shows a change with time in the tumor volume. The mouse administered with CVA11 type showed a suppression of the increase of the tumor volume in comparison with the control, and did not show an adverse event. Since CVA11 type showed an antitumor effect to WiDr in a biological body, it is indicated that the pharmaceutical composition containing CVA11 type has an antitumor effect to oxaliplatin resistant tumors.

Based on the above-explained respective examples, the cancer-cell killing effect of EV4 type to small cell lung cancer, non-small cell lung cancer, colorectal cancer, pancreatic cancer, and esophageal cancer/epidermoid cancer cell lines was confirmed. As to CVA11 type, the cancer-cell killing effect to small cell lung cancer, non-small cell lung cancer, lung squamous cell carcinoma, colorectal cancer, malignant mesothelioma, esophageal cancer/epidermoid cancer, hypopharynx cancer, human-B-lymphocyte tumor, breast cancer, and cervical cancer was confirmed. EV4 type showed an apparent tumor regression performance in CDDP resistant human esophageal cancer model mice. Conversely, CVA11 type showed an apparent tumor regression performance in oxaliplatin resistant human colorectal cancer model mice.

In addition, no serious adverse event was observed in tests with cancer bearing mice, and a body weight reduction was not observed. Hence, it is indicated that EV4 type and CVA11 type have a high safeness. As explained above, EV4 type and CVA11 type are hardly detected in aseptic meningitis in which enteroviruses are likely to be detected. Based on those facts, although EV4 type and CVA11 type are enteroviruses like CV A21 type, EV 6 type, EV 11 type, and the like having a problem in safeness, but because of the intensive antitumor effect and the high safeness, EV4 type and CVA11 type are suitable for an application to a pharmaceutical composition for tumor lysis virus therapies.

The present disclosure can permit various embodiments and modifications without departing from the broadest scope and spirit of the present disclosure. The above-explained embodiments are to explain the present disclosure, and are not intended to limit the scope of the present disclosure. That is, the scope of the present disclosure should be indicated by the appended claims rather than the embodiments. Various modifications carried out within the scope of the appended claims and within the equivalent range thereto should be within the scope of the present disclosure.

This application is based on Japanese Patent Application No. 2012-096088 filed on Apr. 19, 2012. The entire specification, claims, and drawings of Japanese Patent Application No. 2012-096088 are herein incorporated in this specification by reference.

INDUSTRIAL APPLICABILITY

The present disclosure is suitable for a pharmaceutical composition. By applying the present disclosure, it is expected that the prognosis of cancer patients in clinical sites is remarkably improved.

The invention claimed is:

1. A pharmaceutical composition containing a coxsackievirus A11 type that infects cancer cells or an echovirus 4 type that infects cancer cells, wherein the coxsackievirus A11 type or the echovirus 4 type has capsid eliminated.

2. The pharmaceutical composition according to claim 1 further comprising a phosphoinositol-3-kinase inhibitor.

3. The pharmaceutical composition according to claim 1 further comprising an MAP kinase kinase inhibitor.

4. The pharmaceutical composition according to claim 1 further comprising an anticancer agent.

5. The pharmaceutical composition according to claim 1, containing the coxsackievirus A11 type, and utilized for a therapy of a gefitinib resistant or oxaliplatin resistant cancer.

6. The pharmaceutical composition according to claim 1, containing the coxsackievirus A11 type,
wherein the cancer cell is a cancer stem cell.

7. The pharmaceutical composition according to claim 1, containing the coxsackievirus A11 type,
wherein the cancer cell is a cell of cancer selected from the group consisting of small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, breast cancer and cervical cancer.

8. The pharmaceutical composition according to claim 1, containing the echovirus 4 type,
wherein the cancer cell is a cell of cancer selected from the group consisting of, small cell lung cancer, non-small cell lung cancer, colorectal cancer, colon/rectum cancer, pancreatic cancer, and esophageal cancer.

9. A pharmaceutical composition containing cDNA corresponding to the base sequence of the virus RNA of a coxsackievirus A11 type that infects cancer cells or cDNA corresponding to the base sequence of the virus RNA of an echovirus 4 type that infects cancer cells, and an MAP kinase kinase inhibitor.

10. A pharmaceutical composition containing a coxsackievirus A11 type that infects cancer cells or an echovirus 4 type that infects cancer cells, and an MAP kinase kinase inhibitor.

11. The pharmaceutical composition according to claim 10 further comprising an anticancer agent.

12. The pharmaceutical composition according to claim 10, containing the coxsackievirus A11 type, and utilized for a therapy of a gefitinib resistant or oxaliplatin resistant cancer.

13. The pharmaceutical composition according to claim 10, containing the coxsackievirus A11 type,
wherein the cancer cell is a cancer stem cell.

14. The pharmaceutical composition according to claim 10, containing the coxsackievirus A11 type,
wherein the cancer cell is a cell of cancer selected from the group consisting of small cell lung cancer, non-small cell lung cancer, lung squamous cell carcinoma, malignant mesothelioma, colorectal cancer, colon/rectum cancer, esophageal cancer, hypopharynx cancer, human-B-lymphocyte tumor, breast cancer and cervical cancer.

15. The pharmaceutical composition according to claim 10, containing the echovirus 4 type,
wherein the cancer cell is a cell of cancer selected from the group consisting of, small cell lung cancer, non-small cell lung cancer, colorectal cancer, colon/rectum cancer, pancreatic cancer, and esophageal cancer.

* * * * *

SEQUENCE LISTING

```
<160> NUMBER OF SEQ ID NOS: 2

<210> SEQ ID NO 1
<211> LENGTH: 7453
<212> TYPE: DNA
<213> ORGANISM: Coxsackievirus A11

<400> SEQUENCE: 1
ttaaaacagc tgtggggttg ttcccacccc agaggcccac gtggcggcta gtactccggt      60
atcacggtac ccttgtacgc ctgttttata ctccctcccc cgtaacttag aagcaatcaa     120
atcaagttca ataggagggg gtacaaacca gtaccaccac gaacgagcac ttctgtttcc     180
ccggtgaagt tgcatagact gttaccacgg ttgaaagcga ccgatccgtt atccgctcat     240
gtacttcgag aagcctagta cctccttgga atcttcgatg cgttgcgctc agcactcaac     300
cccggagtgt agcttaggct gatgagtctg gacagccctc accggcgacg gtggtccagg     360
ctgcgttggc ggcctacctg tggcccaaag ccacaggacg ctagttgtga acaaggtgtg     420
```

```
aagagcctat tgagctacat gagagtcctc cggcccctga atgcggctaa tcctaaccac    480
ggagcaggcg atcgcaaacc agcaattagc ctgtcgtaac gcgaaagtct gtggcggaac    540
cgactacttt gggtgaccgt gtttctctta tttttattca tggctgctta tggtgacaat    600
catagattgt tatcataaag cgagttggat tggccatccg gtaaaagtca agtatatcat    660
ttacttgttt gtaggattta ttcctttgaa cgtccattta ctcaatctta tcagagtcac    720
attactagta agatctcact atcacaatgg gagctcaagt atcatctcag aaagtgggtg    780
cccatgaaaa caccaatgtg gccaccggtg ggtcaactgt aaactacact actattaatt    840
actacaaaga ctcagctagt aacgctgctt ctaaacagga cttctcccag gacccatcaa    900
aatttactga gcctgttaaa gacatcatgc tcaagtcagc ccctgctcta aactcaccca    960
atattgaggc atgcgggtat agtgataggg tgatgcagtt gactcttggg aattccacca   1020
ttactacaca ggaagcagcc aattcagtgg tagcatacgg tgagtggccg tcttatttgt   1080
cagacaaaga ggctaacccg gttgaccagc aacggagcc cgaagtgtct gcatgcagat   1140
tctacacgtt agatacagtc acgtggagta agagttcaaa aggatggtgg tggaaactac   1200
cggatgcact caaagacatg gggttgttcg ggcaaaacat gtactaccac tacctgggcc   1260
gttcgggcta cactgtgcat gtgcaatgta atgcatccaa gttccaccag ggcgctttgg   1320
gcgttttcgc cattccagag tactgtatgg cctgcaacac tgatgctaag accaactatg   1380
ttagctatgt acaagcaaac ccaggtgagg ctggtggagt ctttaccgac atgtacaatc   1440
ccagttcaga acaactgggg gcacgaaagt ttgcagcggt ggattacctg cttggttgtg   1500
gagtgttggc tggtaacgct ttcgtcttcc cccaccaaat catcaatctc cgcaccaaca   1560
actgtgctac actagttta ccttacgtga actcaatggc aattgattgt atggcaaaac   1620
acaacaattg gggaatagca atactacctc ttgctgagct ggactttgct gaggcgtcat   1680
ctcctgaaat ccccataacc atcacaatcg caccgatgtg ttgtgagttc aatggactga   1740
ggaatttgac tagtccagct aaacagggcc taccagtaat gaatgtacct ggtagtaatc   1800
agttcttatc atctgacaat ttccaatcac cgtgtgcctt acctgagttt gacgtaacac   1860
caccgataca cattccaggt gaagttagga acatgatgga gcttgccgaa atagatacct   1920
taattccaat ggatctcagc gaatccaaga aaaacacaat gggaatgtac agagttgagt   1980
tagggtctgg caagtcacta tctaaaccca tactgtgtct tagcttgagt ccagctagtg   2040
aacaacgttt agggtacacc atgttgggag agattctgaa ttactataca cactggagtg   2100
ggtctttgaa attcaccttt ctgttctgtg ggagcatgat ggcaacaggc aagatttta   2160 tatcgtatgc accaccaggt gcgaaaccac ctacaaccag aagggaggcc atgcttggca   2220
cacacgtgat ttgggacatt ggacttcagt catccgcgac catggtcgtg ccttggatca   2280
gtaacgttat gtaccggagg tgtgtgaagg atgactttac tgaaggtgga tatatatcaa   2340
tgttctacca gactaaaatc gtggtgcctc tatcaacacc caccaatg acactactca   2400 gctttgtgtc agcatgcaac gactttaccg tgcggttgtt gagagacacc acccacatct   2460
cccaaacaac gaaaatcaac actcaagggc aatagaaga aatcatctca actgttgcca   2520
gtaacgcgtt ggcgctcagt caacccaagc cagtggacaa ctctgtacaa acacccaac   2580 aaagtgctcc agtgcatagc caggaggtgc cagcattgac cgcagtggag acaggggcga   2640
caagtgatgt ggttccatct gacctaattc agactagaca cgtattgaat gttaaatcca   2700
ggtctgaatc caccatcgag tcatttttg caagagctgc atgtgtaacc attatgcagg   2760
```

```
tggacaattt caacgcaacc tctgtggaag acaaaagaaa gttgtttgct aaatgggcaa    2820
tcacctacac tgataccgtc cagctgagac ggaaattaga gttttcact tattctagat     2880 ttgacttaga gatgactttt gtgctaactg agagatacta ctcccaaagc tcagggcatg    2940
ctagatctca ggtgtaccaa attatgtatg ttccaccagg ggcacccacg cctagtgcat    3000
gggacgacta cacatggcaa acatcctcca acccatccat tttctttacc accggcaatg    3060
caccaccgcg catttcaatt ccatttgttg gaatcgccaa tgcatactca cacttttatg    3120
atggctttag tagagtacct ttggagggag aaacaacaga cacaggagac gcttactacg    3180
ggctcacttc aataaacgat tttggtacac ttgcagtcag ggtagttaat gactacaacc    3240
cagccagggt ggagacaagg attagagtat acatgaagcc caaacatgtg agagtctggt    3300
gcccgcgacc tccaagagcg gtaagctaca gaggacctgg agtcgacctc ctatcaacat    3360
cagtaacacc tttatccaaa catgacctag cgacatacgg gtttggccac cagaacaaag    3420
cagtttacac agcagggtat aagatttgca actaccacct agctaccag gaagacatgc     3480 agaacgcagt gagcatcatg tggaatagag atctcttgat cgccgagtca aaggctcagg    3540
gtattgactc aatagccagg tgtaattgca atacaggtgt atattattgt gagtctagga    3600
gaaagtacta cccaatttcc tttgtggggc caaccttcca atacatggag ccaacgatt     3660 actaccctgc aaggtatcaa tcacacatgc taatagggca cggttttgca tcaccaggcg    3720
attgtggtgg cattctcaga tgtcaacatg gagtcatagg attgataact gccgggggcg    3780
agggcctagt tgcattctcg gacatcagag atttatatgc atatgaagag gaagccatgg    3840
agcaaggaat ctcgaactac attgagtcac tagggggctgc atttggcagc gggtttactc    3900
aacagattgg agataaaata tcagagctta ccagtatggt caccagcacg atcactgaaa    3960
aattacttaa aaacttgatc aaaattatct cgtctcttgt catcatcacc agaaattatg    4020
aggacaccac cacggtgctc gccaccttgg cactcctcgg ctgtgacgtt tctccatggc    4080
aatggctgaa gaagaaagca tgtgacatct tagaaatccc ctatgttgta aggcaaggtg    4140
atagttggct gaagaaattc accgaggcgt gcaacgcagc taaaggcctg gagtgggtgt    4200
caaacaagat ttctaagttt atagactggc tcaaggaaag gatcattcca caagctagag    4260
ataaacttga gttcgtcact aagcttaagc agctggagat gctagagaat cagattgcta    4320
ccatacacca atcttgtccc agccaagagc atcaggagat tctgttcaat aatgtacgtt    4380
ggttgtcgat ccaatccaaa agatttgcac ctttgtatgc acttgaggcc aaaagaatcc    4440
aaaagttgga acacaccatt aacaactaca tacagttcaa gagcaaacac cgtattgaac    4500
cagtatgttt actagtgcat ggtagtccag gaacaggcaa gtcagttgca acaaatttaa    4560
tagctagagc aattgctgag aaagagaaca cttcaacata ctcgctacca cccgacccctt    4620 cacactttga tggwtacaaa cagcagggag tggtaatcat ggacgacctc aatcagaacc    4680
ctgatggggc tgacatgaaa ctattctgtc agatggtgtc tacagttgaa tttatcccac    4740
caatggcatc tttagaagag aaaggcattc tgtttacgtc caactatgtg ctagcttcca    4800
ccaactccag tcggattgca ccacctactg tagcccatag tgatgcacta gccaggaggt    4860
ttgcctttga catagatatt caggtcatga atgagtactc cagagatgga agcttaata     4920 tggcaatggc tacggagatg tgcaagaact gccaccaacc agcaaacttc aagagatgct    4980
gtcctctggt gtgcggaaaa gcaattcagt taatggataa gtcatcaaga gtcaggtata    5040
gtgtggatca gattactact atgatcatca atgaaaggaa tagaagatca aatattggca    5100
attgtatgga agcactcttc caaggaccac tccagtacaa agacttgaaa attgacatta    5160
```

```
aaacaacacc accccccagag tgcatcaatg atttgctcca ggcagttgac tcccaagagg   5220
ttagggacta ttgtgagaag aaagggtgga ttgtcaatat caccagtcaa gtccaaactg   5280
aaaggaacat caatagagct atgacaattc tgcaagctgt cacaacattt gctgcggtgg   5340
ccggagttgt gtacgtcatg tacaaacttt tcgctggata tcaaggagct acaccggcc    5400 tcccgaacaa aagacctagc gtacctacca ttagaactgc taaggtgcag ggtccaggct   5460
tcgactacgc agtcgcaatg gctaaaagaa acatagttac tgctaccacc agtaaggggg   5520
aatttaccat gctaggagtt catgacaatg tggcgatttt accaactcat gcgtcgcctg   5580
gagagagcat tgtgattgat ggaaaagagg tggagatttt agatgcaaag gctcttgaag   5640
accaagcagg cacaaatctg gaaattacaa ttataacact gaaagaaat gaaaaattca    5700 gagacattag accacacatt cccacacaga ttactgagac taacgatgga gtgctgatcg   5760
tgaacactag taagtatccc aacatgtatg tgcctgttgg tgctgtgacc gaacagggat   5820
atcttaatct cggtgggcgt caaacagctc gtacattaat gtacaatttc ccaactagag   5880
cgggccagtg tggtggagtt gtcacttgca ctggtaaggt catcgggatg catgttggtg   5940
ggaatggttc acatgggttc gcagcggccc taaagcgatc gtatttcact cagagtcaag   6000
gtgagattca gtggataaga ccatcaaaag aagtggggtta ccccatcatt aatgctcctt   6060
ccaagactaa attagaacct agtgcctttc attatgtgtt tgagggagtc aaagagccag   6120
cagtccttac taagaatgac cctagactaa aaacagattt tgaagaggcc attttctcaa   6180
aatacgtagg gaacaaaatc acggaagtag atgaatacat gaaggaagca gtagaccact   6240
atgcgggaca actactttcc ctagacatca acacagacca gatgtgcctt gaggatgcca   6300
tgtacggcac tgatgggctt gaagctttgg acctcagtac tagtgcaggc taccttatg    6360 ttgccatggg aaagaaaag agggacattc taaataaaca aaccagggat accaaggaga   6420
tgcagagatt actcgacacc tatggaatta atctacctct agttacttat gtaaaagatg   6480
aactcaggtc taagacaaaa gtggaacaag gtaaatctag gctaattgaa gcatccagtc   6540
tcaatgattc agttgcaatg agaatggcct ttggtaactt gtatgcagca ttccacaaaa   6600
acccaggtgt ggtgacagga tctgcagttg ggtgcgaccc agacctgttc tggagtaaga   6660
taccagtgct aatggaagaa aaactctttg ctttcgatta cacgggatat gatgcatcac   6720
tcagtcccgc ttggttcgaa gctttgaaaa tggttttgga gaaaattggt tttgagata    6780 gggtagatta cattgactac ttgaatcact cacaccactt atacaaaaac aaaacttatt   6840
gtgttaaggg tggtatgcca tctggctgct ctggcacttc aatcttcaac tcaatgatca   6900
acaatttgat tatcaggacg ctcttactga aaacctacaa gggcatagat ttagatcacc   6960
taaaaatgat tgcctatggt gatgatgtaa ttgcttctta ccccccatgag gttgacgcta   7020 gtctcctagc ccaatcagga aaagactatg gactaaccat gactccagca gacaagtcag   7080
ctacattcga aacagtcaca tgggagaacg taacattctt gaaaagattc ttcagagcag   7140
atgaaaagta ccccttctg atacatccag tgatgccaat gaaggaaatt catgaatcaa   7200
ttagatggac taaagatccc agaaacaccc aggatcatgt gcgctcatta tgcctattgg   7260
cttggcataa tggcgaagag gagtataaca aattttagc tagaattaga agtgtgccaa    7320
ttggaagagc attattgctc cctgagtact ctacattgta ccgccgttgg cttgactcat   7380
tctagtaacc ctacctcagt cgaattggat tgggtgatac tgatgtaggg gtaaattttt   7440
ctttaattcg gag                                                      7453
```

<210> SEQ ID NO 2
<211> LENGTH: 2547
<212> TYPE: DNA
<213> ORGANISM: Echovirus E4

<400> SEQUENCE: 2

```
atgggagctc aagtgtcaac gcaaaaaaca ggagcccacg agaccggatt gaacgcaagt     60
ggtaactcga tcatccacta cacgaacatt aattattaca aagatgcagc atccaattcg    120
gcaaaccggc aggattttac acaggaccca agcaaattta cagaaccagt taaggacgtc    180
atgatcaagt ctttaccagc gctgaactcc cccaccgtag aggaatgcgg ttacagtgac    240
cgtgttagat ccataacact agggaactct acgatcacaa cccaagagtg cgctaatgta    300
gtggttgcgt atggtgtgtg gcctgagtac ctgaaagatg ctgaggccac agcagaagat    360
caacccaccc aaccagacgt ggcgacgtgc aggttctaca cactagattc agttgagtgg    420
caaaagaact caccaggatg gtggtggaaa ttccctgatg cgttgaatga tatgggtctg    480
tttggacaga atatgttgta ccactatcta ggaagaacag gatacactat acatgttcag    540
tgtaacgcct cgaagtttca ccaagggtgc atactcgtgg tgtgtgtacc ggaggctgaa    600
atggggtgta cgcagacaga taaaactgtt aatcaagaac atttgagcca aggcgagaga    660
gccatgagtt tcaaggacag taccacaggc gatgaaaact ctgtgcaggc tgctgtgtgg    720
aatgcaggac taggcgttgg tgtgggcaat ttgacaatat ttccgcatca atggataaac    780
ctacgcacta ataacagtgc gaccatagtg atgccataca taaactgcgt tcccatggac    840
aatatgttta gacaccaaaa cttcactctc atgttgatcc cgtttgttcc ccttgattac    900
agtgatggtg cctccagcta cgttcccatt acggttacag tggcccccat gtgcgctgaa    960
tacaacggac ttaggttggc aggtaaacaa ggcttgccaa caatgcttac cccaggtagt   1020
aaccagttcc ttacatcaga tgattttcaa tcaccgtcgg ccatgccgca atttgatgtg   1080
accccagaaa tgaacatccc aggtgaggtg aagaacttga tggagatcgc agaagtggac   1140
tctgtggttc cagtcaacaa cgttgaagac gccatcaact ccatggcagc atacagaatt   1200
gaggtcaata catcgaagca cgcaggcgac caggtttttg gatttaaact ggacccgggg   1260
tcagatgccg tgttaaatag aacattactc ggtgaaatca tgaattacta cacccactgg   1320
tcaggcagca taaagttaac atttgttttc tgtggttcag ccatgaccac cggtaagttc   1380
ctcttgtctt acgcaccacc aggggcgggg gcacctgcta agcgtaaaga cgccatgcta   1440
ggaacacatg tagtgtggga tgtgggatta caatcaagtt gcgtcttgtg tatcccatgg   1500
ataagccaag cgcactacag gtttgtggag aaggacccgt actcagcagc ggggtacgtg   1560
acctgttggt accagactgg agtggtgtcc ccggccggaa accagccaaa gtgttacatc   1620
atgtgctttg tgtcagcgtg taatgatttc tcagtacgat tgctgcgcga cactaaattt   1680
atttctcaaa gcaatttcta tcaaggagat gtgcaggacg cagtggctgg ggccatagtg   1740
cgtgtggcta atactctccc atcaggcccc tcaaacaatg aggctatacc caacttaaca   1800
gccgtagaaa ctggacacac ctcgcaggtg acaccgggtg atacaatgca gacgcgccac   1860
gtagtgaaca tgcacactcg ttctgagtcg tcaatcgaga acttcctggc gcggtcagca   1920
tgtgtatact acctcgatta ccgaacagga acggggcctg gcaatcaata ctttagccag   1980
tggactatta ccacaagacg agttgcgcag ctgcgtcgaa aattggagat gttcacctat   2040
ctaaggttcg acatggagat cacgattgta ataacgagtt cacaagatca gcctaccgtc   2100
cgaaacccag acacaccggt cttgacacac caaatcatgt atgtgccacc aggagggcca   2160
```

```
atcccagcaa aggtcgacga ttactgttgg caaacatcca caaacoccag tgtcttctgg    2220 actgaaggga acgcaccagc ccggatatcc atcccgttca tcagtgtcgg gaatgcatat    2280
agtagtttct acgatggatg gtcaaatttc tcgcaaaatg ggcggtatgg ctacaacacc    2340
ctgaacaaca tggggcaatt gtttttcagg catgtcaata aacccagtcc caacactgtc    2400
acaagtgttg cccgcatata cttcaagccc aaacacgtga aggcatgggt cccgcgacca    2460
ccgcgattgt gcccttacat taatgctgga gatgtaaatt tcaccccac atcggtcact     2520 gagaagcgag cgagcctgat aaccaca                                        2547
```